(12) United States Patent
Famoso

(10) Patent No.: US 12,364,225 B2
(45) Date of Patent: Jul. 22, 2025

US012364225B2

(54) RICE CULTIVAR DESIGNATED 'ADDI JO'

(71) Applicant: Board of Supervisors of Louisiana State University and Agricultural and Mechanical College, Baton Rouge, LA (US)

(72) Inventor: Adam Famoso, Lafayette, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 240 days.

(21) Appl. No.: 18/082,625

(22) Filed: Dec. 16, 2022

(65) Prior Publication Data

US 2024/0196827 A1  Jun. 20, 2024

(51) Int. Cl.
*A01H 6/46* (2018.01)
*A01H 5/10* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS 9,686,932 B2 * 6/2017 De Mattos ............... A01H 5/10
12,137,654 B2 * 11/2024 Redoña .............. C12N 15/8278

OTHER PUBLICATIONS

Schnell et al (A comparative analysis of insertional effects in genetically engineered plants: considerations for pre-market assessments. Transgenic research 24: 1-17, 2015) (Year: 2015).*
Sun et al (Comparison of the Phenotypic Performance, Molecular Diversity, and Proteomics in Transgenic Rice. Plants. p. 1-22, 2022) (Year: 2022).*
LSU releases two long-grain rice varieties_Jan. 2022 (Year: 2022).*
MSU_'Thad'_2016 (Year: 2016).*
LSU_'Catahoula' _2009 (Year: 2009).*
"Industry News," Rice Farming (Mar. 2022).
109th Annual Research Report, H. Rouse Caffey Rice Research Station 2017, pp. 90-92 (published May 2018).
113th Annual Research Report, H. Rouse Caffey Rice Research Station 2021, pp. 32, 35, 37 40, 43, 45, 47, 49, 90, 103, 151-154, 155, 162, 163, 171, 423, 425 (published Sep. 2022).
A. Famoso, Oct. 20, 2020 presentation to the 2020 USA Rice Grain Quality Symposium.
A. Famoso, "New Rice Varieties from the LSU AgCenter," H. Rouse Caffey Rice Research Station News vol. 19, issue 1, pp. 1-2 (Feb. 2022).
A. Famoso, 2022 Louisiana Rice Research Board Project Proposals (Nov. 10, 2021).
B. Schultz, Breeders developing lines for Latin American tastes (press release Nov. 24, 2020).
D. Albert, "New varieties, new faculty highlight 113th LSU AgCenter Rice Field Day" (press release Jul. 18, 2022).
D. Albert, LSU AgCenter rice breeding program progresses new varieties, monitors PVL03 (press release Jun. 25, 2022).
D. Albert, "Growers' interests prompt advance of conventional rice varieties" (press release Dec. 15, 2021).
D. Albert, "Rice breeding program advancing lines with unique grain qualities" (press release, Nov. 21, 2022).
B. Angira et al., LSU Ag: Breeding rice for Latin American export markets, Houma Times (Jun. 29, 2022).
Mississippi State University, "Notice of Release of 'Thad' Rice" (2016).
USA Rice, "New U.S. Rice Variety Customized for Latin American Consumers," press release (Apr. 15, 2021).
S. Blanche et al., "Registration of 'Catahoula' Rice," J. Plant Reg.,, vol. 3, pp. 146-149 (2009).
V. Boyd, "LSU releases an early, high-yielding long grain and a high-amylose long grain for parboiling and export markets," Rice Farming (Jan. 15, 2022).
"Plant Variety License between the Louisiana State University AgCenter and Supreme Rice, LLC" (Sep. 2022).

* cited by examiner

*Primary Examiner* — Charles Logsdon
*Assistant Examiner* — Wayne Zhong
(74) *Attorney, Agent, or Firm* — John H. Runnels

(57) ABSTRACT

The rice cultivar designated 'Addi Jo' and its hybrids and derivatives are disclosed.

17 Claims, No Drawings

RICE CULTIVAR DESIGNATED 'ADDI JO'

TECHNICAL FIELD

This invention pertains to the rice cultivar designated 'Addi Jo,' and to hybrids of, and cultivars derived from the rice cultivar designated 'Addi Jo.'

BACKGROUND ART

Rice is an ancient agricultural crop, and remains one of the world's principal food crops. There are two cultivated species of rice: *Oryza sativa* L., the Asian rice, and *O. glaberrima* Steud., the African rice. *Oryza sativa* L. constitutes virtually all of the world's cultivated rice and is the species grown in the United States. The three major rice-producing regions in the United States are the Mississippi Delta (Arkansas, Mississippi, northeast Louisiana, southeast Missouri), the Gulf Coast (southwest Louisiana, southeast Texas); and the Central Valley of California. See generally U.S. Pat. No. 6,911,589.

Rice is a semiaquatic crop that benefits from flooded soil conditions during part or all of the growing season. In the United States, rice is typically grown on flooded soil to optimize grain yields. Heavy clay soils or silt loam soils with hard pan layers about 30 cm below the surface are typical rice-producing soils, because they reduce water loss from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination comes from irrigation or rainfall. Another method of dry-seeding is to broadcast the seed by airplane into a flooded field, and then promptly drain the water from the field. For the dry-seeded system, when the plants have reached sufficient size (four- to five-leaf stage), a shallow permanent flood of water 5 to 16 cm deep is applied to the field for the remainder of the crop season. Some rice is grown in upland production systems, without flooding.

One method of water-seeding is to soak rice seed for 12 to 36 hours to initiate germination, and then to broadcast the seed by airplane into a flooded field. The seedlings emerge through a shallow flood, or the water may be drained from the field for a short time to enhance seedling establishment. A shallow flood is then maintained until the rice approaches maturity. For both the dry-seeded and water-seeded production systems, the fields are drained when the crop is mature, and the rice is harvested 2 to 3 weeks later with large combines.

In rice breeding programs, breeders typically use the same production systems that predominate in the region. Thus, a drill-seeded breeding nursery is typically used by breeders in a region where rice is drill-seeded, and a water-seeded nursery is typically used in regions where water-seeding prevails.

Rice in the United States is classified into three primary market types by grain size, shape, and endosperm composition: long-grain, medium-grain, and short-grain. Long-grain cultivars have been traditionally grown in the southern states and generally receive higher market prices in the U.S.

Although specific breeding objectives vary somewhat in different regions, increasing yield is a primary objective in most programs. Grain yield depends, in part, on the number of panicles per unit area, the number of fertile florets per panicle, and grain weight per floret. Increases in any or all of these components may help improve yields. Heritable variation exists for each of these components, and breeders may directly or indirectly select for any of them. A specialty rice may, however, be an acceptable for niche markets even with somewhat lower yields than other contemporaneous cultivars.

There are numerous steps in the development of any novel, desirable plant germplasm. Plant breeding begins with the analysis and definition of problems and weaknesses of the current germplasm, the establishment of program goals, and the definition of specific breeding objectives. The next step is selection (or generation) of germplasm that possesses the desired traits to meet the program goals. A goal is often to combine in a single variety an improved combination of desirable traits from two or more ancestral germplasm lines. These traits may include such things as higher seed yield, resistance to disease or insects, better stems and roots, tolerance to low temperatures, and better agronomic characteristics or grain quality.

The choice of breeding and selection methods depends on the mode of plant reproduction, the heritability of the trait(s) being improved, and the type of seed that is used commercially (e.g., $F_1$ hybrid, versus pure line or inbred cultivars). For highly heritable traits, a choice of superior individual plants evaluated at a single location may sometimes be effective, while for traits with low or more complex heritability, selection is often based on mean values obtained from replicated evaluations of families of related plants. Selection methods include pedigree selection, modified pedigree selection, mass selection, recurrent selection, and combinations of these methods.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively-inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s), typically for three or more years. The best lines become candidates for new commercial cultivars; those still deficient in a few traits may be used as parents to produce new populations for further selection.

These processes, which lead ultimately to marketing and distribution of new cultivars or hybrids, typically take 8 to 12 years from the time of the first cross; they may further rely on (and be delayed by) the development of improved breeding lines as precursors. Development of new cultivars and hybrids is a time-consuming process that requires precise forward planning and efficient use of resources. There are never assurances of a successful outcome.

A particularly difficult task is the identification of individual plants that are, indeed, genetically superior. A plant's phenotype results from a complex interaction of genetics and environment. One method for identifying a genetically superior plant is to observe its performance relative to other experimental plants and to a widely grown standard cultivar raised in an identical environment. Repeated observations from multiple locations can help provide a better estimate of genetic worth.

The goal of rice breeding is to develop new, unique, and superior rice cultivars and hybrids. The breeder initially selects and crosses two or more parental lines, followed by self-pollination and selection, producing many new genetic combinations. The breeder can generate billions of different genetic combinations via crossing, selfing, and mutation breeding. The traditional breeder has no direct control of genetics at the molecular level. Therefore, two traditional breeders working independently of one another will never develop the same line, or even very similar lines, with the same traits.

Each year, the plant breeder selects germplasm to advance to the next generation. This germplasm is grown under different geographical, climatic, and soil conditions. Further selections are then made, during and at the end of the growing season. The resulting cultivars (or hybrids) and their characteristics are inherently unpredictable. This is because the traditional breeder's selection occurs in unique environments, with no control at the molecular level, and with potentially billions of different possible genetic combinations being generated. A breeder cannot predict the final resulting line, except possibly in a very gross and generic fashion. Further, the same breeder may not produce the same cultivar twice, even starting with the same parental lines, using the same selection techniques. This uncontrollable variation results in substantial effort and expenditures in developing superior new rice cultivars (or hybrids); and makes each new cultivar (or hybrid) novel and unpredictable.

The selection of superior hybrid crosses is conducted slightly differently. Hybrid seed is typically produced by manual crosses between selected male-fertile parents or by using genetic male sterility systems. These hybrids are typically selected for single gene traits that unambiguously indicate that a plant is indeed an $F_1$ hybrid that has inherited traits from both presumptive parents, particularly the male parent (since rice normally self-fertilizes). Such traits might include, for example, a semi dwarf plant type, pubescence, awns, or apiculus color. Additional data on parental lines, as well as the phenotype of the hybrid, influence the breeder's decision whether to continue with a particular hybrid cross or an analogous cross, using related parental lines.

Pedigree breeding and recurrent selection breeding methods are sometimes used to develop cultivars from breeding populations. These breeding methods combine desirable traits from two or more cultivars or other germplasm sources into breeding pools from which cultivars are developed by selfing and selection of desired phenotypes. The new cultivars are evaluated to determine commercial potential.

Pedigree breeding is often used to improve self-pollinating crops. Two parents possessing favorable, complementary traits are crossed to produce $F_1$ plants. An $F_2$ population is produced by selfing one or more $F_1$s. Selection of the superior individual plants may begin in the $F_2$ (or later) generation. Then, beginning in the $F_3$ (or other subsequent) generation, individual plants are selected. Replicated testing of panicle rows from the selected plants can begin in the $F_4$ (or other subsequent) generation, both to fix the desired traits and to improve the effectiveness of selection for traits that have low heritability. At an advanced stage of inbreeding (e.g., $F_6$ or $F_7$), the best lines or mixtures of phenotypically-similar lines are tested for potential release as new cultivars.

Mass and recurrent selection methods can also be used to improve populations of either self- or cross-pollinating crops. A genetically variable population of heterozygous individuals is either identified or created by intercrossing several different parents. The best offspring plants are selected based on individual superiority, outstanding progeny, or excellent combining ability. The selected plants are intercrossed to produce a new population in which further cycles of selection are continued.

Backcross breeding is often used to transfer genes for a simply inherited, highly heritable trait into a desirable homozygous cultivar or inbred line, which is the recurrent parent. The source of the trait to be transferred is called the donor parent. The resulting plant should ideally have the attributes of the recurrent parent (e.g., cultivar) and the desired new trait transferred from the donor parent. After the initial cross, individuals possessing the desired donor phenotype (e.g., disease resistance, insect resistance, herbicide tolerance) are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ generation to the desired level of inbreeding, the several plants from which the lines are derived will each trace to different $F_2$ individuals. The number of plants in a population declines each generation, due to failure of some seeds to germinate or the failure of some plants to produce at least one seed. As a result, not all of the $F_2$ plants originally sampled in the population will be represented by progeny in subsequent generations.

In a multiple-seed procedure, the breeder harvests one or more seeds from each plant in a population and threshes them together to form a bulk. Part of the bulk is used to plant the next generation and part is held in reserve. The procedure has been referred to as modified single-seed descent or the pod-bulk technique. The multiple-seed procedure has been used to save labor at harvest. It is considerably faster to thresh panicles by machine than to remove one seed from each by hand as in the single-seed procedure. The multiple-seed procedure also makes it possible to plant the same number of seeds from a population for each generation of inbreeding. Enough seeds are harvested to compensate for plants that did not germinate or produce seed.

Other common and less-common breeding methods are known and used in the art. See, e.g., R. W. Allard, Principles of Plant Breeding (John Wiley and Sons, Inc., New York, New York, 1967); N. W. Simmonds, Principles of Crop Improvement (Longman, London, 1979); J. Sneep et al., Plant Breeding Perspectives (Pudoc, Wageningen, 1979); and W. R. Fehr, Principles of Cultivar Development: Theory and Technique (Macmillan Pub., New York, New York, 1987).

Proper testing should detect any major faults and establish the level of superiority or improvement over current cultivars. In addition to showing superior performance, there must be a demand for a new cultivar or hybrid; i.e., the new cultivar or hybrid should either be compatible with industry standards, or it should create a new market. The introduction of a new cultivar or hybrid may incur additional costs to the seed producer, the grower, processor, and consumer for such things as special advertising and marketing, altered seed and commercial production practices, and new product utilization. The testing that precedes the release of a new cultivar or hybrid should take into account research and development costs, in addition to technical superiority of the final cultivar or hybrid.

High amylose rice varieties are preferred for some export markets for their non-sticky cooking characteristics. For example, Latin American importers and consumers tend to prefer nonsticky rice. Latin American rice varieties typically have higher amylose content as compared to U.S. long-grain varieties. Higher amylose levels contribute to the nonsticky cooking quality of the rice.

High amylose rice is also desirable for some processed foods and parboiled rice products. However, prior high-amylose rice varieties have typically been susceptible to blast disease. There is an unfilled need for high-amylose rice varieties that are resistant to blast disease, particularly (but not limited to) varieties that are well-adapted for growth in the southern United States.

See A. Famoso, presentation given at an Oct. 20, 2020 presentation to the 2020 USA Rice Grain Quality Symposium. "LA2126: Long Grain Conventional" was mentioned on one of the slides, along with some of its characteristics. However, no outside party was given access to or samples of any plants or seeds.

USA Rice, "New U.S. Rice Variety Customized for Latin American Consumers," press release (Apr. 15, 2021) mentioned LA2126 as an experimental line developed especially for Latin American consumers. The press release mentioned that during a visit to Lafayette, Louisiana in April 2021, 350-gram samples of LA2126 were shared with members of the Costa Rican Rice Millers Association, to evaluate its cooking characteristics (while still in Louisiana). These were in fact samples of milled rice, not of seed rice. No outside party was given access to or samples of any plants or un-milled seeds, only small samples of milled rice.

The LA20-2126 line was mentioned in A. Famoso, "2022 Louisiana Rice Research Board Project Proposals (Nov. 10, 2021); with information concerning some of its characteristics. No outside party was given access to or samples of any plants or seeds.

The inventor and his collaborators have publicly mentioned work involving 'Addi Jo' (or LA2126) at LSU-sponsored growers meetings and field days at various locations on various dates including the LSU Rice Research Station's Annual Field Days on Jul. 1, 2020, Jun. 30, 2021, and Jun. 29, 2022. However, no outside parties were given access to or samples of any plants or seeds.

"Industry News," Rice Farming (March 2022) reported that LA20-2126, named 'Addi Jo,' had been released by LSU. However, no outside parties were given access to or samples of any plants or seeds.

See also D. Albert, "New varieties, new faculty highlight 113th LSU AgCenter Rice Field Day" (press release Jul. 18, 2022); and D. Albert, "LSU AgCenter rice breeding program progresses new varieties, monitors PVL03 (press release Jun. 25, 2022); and D. Albert, "Growers' interests prompt advance of conventional rice varieties" (press release Dec. 15, 2021); and B. Angira et al., "LSU Ag: Breeding rice for Latin American export markets, *Houma Times* (Jun. 29, 2022); and V. Boyd, "LSU releases an early, high-yielding long grain and a high-amylose long grain for parboiling and export markets," *Rice Farming* (Jan. 15, 2022); and D. Albert, "Rice breeding program advancing lines with unique grain qualities" (press release, Nov. 21, 2022); and A. Famoso, "New Rice Varieties from the LSU AgCenter," *H. Rouse Caffey Rice Research Station News* vol. 19, issue 1, pp. 1-2 (February 2022); and B. Schultz, "Breeders developing lines for Latin American tastes (press release Nov. 24, 2020).

See also 109th *Annual Research Report*, H. Rouse Caffey Rice Research Station 2017, pp. 90-92 (published May 2018); and 113th *Annual Research Report*, H. Rouse Caffey Rice Research Station 2021, pp. 32, 35, 37 40, 43, 45, 47, 49, 90, 103, 151-154, 155, 162, 163, 171, 423, 425 (published September 2022).

"Plant Variety License between the Louisiana State University AgCenter and Supreme Rice, LLC" (September 2022) licensed out certain rights in the variety 'Addi Jo.' However, as of the December 2022 provisional filing date, the licensee had not yet been granted access to any plants or seeds Mississippi State University, "Notice of Release of 'Thad' Rice" (2016) describes the development and characteristics of the rice variety 'Thad.'

S. Blanche et al., "Registration of 'Catahoula' Rice," *J. Plant Reg.*, vol. 3, pp. 146-149 (2009) describes the development and characteristics of the rice variety 'Catahoula.'

DISCLOSURE OF THE INVENTION

I have discovered a novel, high-amylose, long-grain rice cultivar designated 'Addi Jo' (former experimental designation LA20-2126). Unlike many other high-amylose varieties, 'Addi Jo' is resistant to blast disease. The grain quality is very good. 'Addi Jo' produces a non-sticky cooked grain that is desired by some importers and end users, particularly in Latin American markets. High amylose rice has slower digestibility, giving it nutritional benefits. 'Addi Jo' has amylose levels comparable to those seen in the varieties Rexmont and Dixiebelle.

This invention also pertains to methods for producing a hybrid or new variety by crossing the rice variety 'Addi Jo' with another rice line, one or more times. Thus any such methods using the rice variety 'Addi Jo' are aspects of this invention, including backcrossing, hybrid production, crosses to populations, and other breeding methods involving 'Addi Jo.' Hybrid plants produced using the rice variety 'Addi Jo' as a parent are also within the scope of this invention. Optionally, either parent can, through routine manipulation of cytoplasmic or other factors through techniques known in the art, be produced in a male-sterile form.

In another embodiment, this invention allows for single-gene converted plants of 'Addi Jo.' The single transferred gene may be a dominant or recessive allele. Preferably, the single transferred gene confers a trait such as resistance to insects; resistance to one or more bacterial, fungal, or viral diseases; male fertility or sterility; enhanced nutritional quality; enhanced processing qualities; or a source of herbicide resistance. The single gene may be a naturally occurring rice gene or a transgene introduced through genetic engineering techniques known in the art. The single gene also may be introduced through traditional backcrossing techniques or genetic transformation techniques known in the art.

In another embodiment, this invention provides regenerable cells for use in tissue culture of rice plant 'Addi Jo.' The tissue culture may allow for regeneration of plants having physiological and morphological characteristics of rice plant 'Addi Jo' and of regenerating plants having substantially the same genotype as rice plant 'Addi Jo.' Tissue culture techniques for rice are known in the art. The regenerable cells in tissue culture may be derived from sources such as embryos, protoplasts, meristematic cells, callus, pollen, leaves, anthers, root tips, flowers, seeds, panicles, or stems. In addition, the invention provides rice plants regenerated from such tissue cultures.

In some embodiments, the present invention provides a method for treating rice. The method comprises contacting the rice with an agronomically acceptable composition, wherein said rice belongs to any of (a) variety 'Addi Jo' or (b) a hybrid, derivative, or progeny of 'Addi Jo,' wherein the agronomically acceptable composition comprises at least one agronomically acceptable active ingredient selected from the group consisting of fungicides, insecticides, antibiotics, stress tolerance-enhancing compounds, growth promoters, herbicides, molluscicides, rodenticides, animal repellants, and combinations thereof.

In other embodiments, the present invention provides an essentially derived variety of the line 'Addi Jo,' where "essentially derived" has the meaning given in Title II, Section 41(a) of the United States Plant Variety Protection Act, i.e. 7 U.S.C. § 2401(a)(4)(A) as amended Dec. 20, 2018, which definition is incorporated in relevant part by reference.

Definitions

The following definitions apply throughout the specification and claims, unless context clearly indicates otherwise:

"Days to 50% heading." Average number of days from seeding to the day when 50% of all panicles are exerted at least partially through the leaf sheath. A measure of maturity.

"Grain Yield." Grain yield is measured in pounds per acre, at 12.0% moisture. Grain yield depends on a number of factors, including the number of panicles per unit area, the number of fertile florets per panicle, and grain weight per floret.

"Lodging Percent." Lodging is a subjectively measured rating, and is the percentage of plant stems leaning or fallen completely to the ground before harvest.

"Grain Length (L)." Length of a rice grain, or average length, measured in millimeters.

"Grain Width (W)." Width of a rice grain, or average width, measured in millimeters.

"Length/Width (L/W) Ratio." This ratio is determined by dividing the average length (L) by the average width (W).

"1000 Grain Wt." The weight of 1000 rice grains, measured in grams.

"Harvest Moisture." The percentage moisture in the grain when harvested.

"Plant Height." Plant height in centimeters, measured from soil surface to the tip of the extended panicle at harvest.

"Apparent Amylose Percent." The percentage of the endosperm starch of milled rice that is amylose. The apparent amylose percent is an important grain characteristic that affects cooking behavior. Standard long grains contain 20 to 23 percent amylose. Rexmont-type long grains contain 24 to 25 percent amylose. Short and medium grains contain 13 to 19 percent amylose. Waxy rice contains zero percent amylose. Amylose values, like most characteristics of rice, depend on the environment. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

"Alkali Spreading Value." An index that measures the extent of disintegration of the milled rice kernel when in contact with dilute alkali solution. It is an indicator of gelatinization temperature. Standard long grains have a 3 to 5 Alkali Spreading Value (intermediate gelatinization temperature).

"Peak Viscosity." The maximum viscosity attained during heating when a standardized, instrument-specific protocol is applied to a defined rice flour-water slurry.

"Trough Viscosity." The minimum viscosity after the peak, normally occurring when the sample starts to cool.

"Final Viscosity." Viscosity at the end of the test or cold paste.

"Breakdown." The peak viscosity minus the hot paste viscosity.

"Setback." Setback 1 is the final viscosity minus the trough viscosity. Setback 2 is the final viscosity minus the peak viscosity.

"RVA Viscosity." Viscosity, as measured by a Rapid Visco Analyzer, a widely used laboratory instrument to examine the paste viscosity or thickening ability of milled rice during the cooking process.

"Hot Paste Viscosity." Viscosity measure of rice flour/water slurry after being heated to 95° C. Lower values indicate softer and stickier cooking types of rice.

"Cool Paste Viscosity." Viscosity measure of rice flour/water slurry after being heated to 95° C. and uniformly cooled to 50° C. Values less than 200 indicate softer cooking types of rice.

"Allele." An allele is any of one or more alternate forms of the same gene. In a diploid cell or organism such as rice, the two alleles of a given gene occupy corresponding loci on a pair of homologous chromosomes.

"Backcrossing." Backcrossing is a process in which a breeder repeatedly crosses hybrid progeny back to one of the parents, for example, crossing a first generation hybrid $F_1$ with one of the parental genotypes of the $F_1$ hybrid, and then crossing a second generation hybrid $F_2$ with the same parental genotype, and so forth.

"Essentially all the physiological and morphological characteristics." A plant having "essentially all the physiological and morphological characteristics" of a specified plant refers to a plant having the same general physiological and morphological characteristics, except for those characteristics that are derived from a particular converted gene.

"Quantitative Trait Loci (QTL)." Quantitative trait loci (QTL) refer to genetic loci that to some degree control numerically measurable traits, generally traits that are continuously distributed.

"Regeneration." Regeneration refers to the development of a plant from tissue culture.

"Single Gene Converted (Conversion)." Single gene converted (conversion) includes plants developed by backcrossing, wherein essentially all of the desired morphological and physiological characteristics of a parental variety are recovered, while also retaining a single gene that is transferred into the plants via crossing and backcrossing. The term can also refer to the introduction of a single gene through genetic engineering techniques known in the art.

MODES FOR CARRYING OUT THE INVENTION

'Addi Jo' (also called LA20-2126 or RU2002126) is a long-grain conventional rice line with a high amylose grain. This grain type results in a non-sticky cooked grain that is desired by some importers and end users. 'Addi Jo' (or LA20-2126) has very good yields and grain quality and is resistant to blast disease. It was developed using a pedigree selection system at the LSU AgCenter's H. Rouse Caffey Rice Research Station (RRS) in Crowley, Louisiana. LA20-2126 was selected from the cross Thad/Catahoula, which was made at the RRS in 2015. Thad is a high-amylose long-grain conventional variety release by the Mississippi State University's Mississippi Agricultural and Forestry Experiment Station in 2016. Catahoula is a long-grain conventional variety released by the LSU AgCenter in 2008. Catahoula contains the broad-spectrum blast resistance gene Pita. LA20-2126 was first tested from the bulk of a single F2:F4 row (1750348) made at the Puerto Rico winter nursery in 2017. LA20-2126 was evaluated under the designation of 181L2027 in 2018 in the conventional Preliminary Yield "PYPR" Trial and in 2019 in the Regional Yield Trial across five locations. In 2020, it was advanced into the Commercial Advanced (CA) and Cooperative Uniform Regional Rice Nurseries (URRN) with the designation RU2002126. 'Addi Jo' and its hybrids and derived varieties are adapted for growing throughout the rice growing areas of Louisiana, Texas, Arkansas, Mississippi, and Missouri; and may also be suited for growing in other rice-producing areas in other countries.

After the initial cross was made, the line was harvested and selected through early generations for phenotypic superiority for characteristics such as short plant architecture, grain shape and uniformity, seedling vigor, tiller number, and grain size. In later generations (during seed increase), the line was selected for uniformity and purity both within and between panicle rows. Variants removed from 'Addi Jo' seed-increase fields were primarily taller or later plants. Other variants removed included those with any one or more of the following: leaf pubescence, earlier, shorter, medium grain, intermediate grain, gold hull, and lighter colored leaf. The overall incidence of variants was less than 1 per 10,000 plants. Foundation seed rice was grown, beginning with the $F_7$ generation. Seed from the $F_5$, $F_6$, and $F_7$ generations was entered into an experimental line testing program, and was also tested at several locations in Louisiana rice producing areas. 'Addi Jo' has been observed to be stable for at least three generations.

TABLE A

Origin and Breeding History of 'Addi Jo' (LA20-2126)
Pedigree - 'Thad' / 'Catahoula'

| Year | Generation | Test (Entry #) |
|---|---|---|
| 2015 | F0 | 'Thad' / 'Catahoula' |
| 2016 | F1 | 16TA086 |
| 2017 | F2 | 17F7118 |
| 2017 | F3 | 17S0348 (Puerto Rico) |
| 2018 | F4 | 18PYPR-027 (181L2027) |
| 2019 | F5 | 19RYT-108 |
| 2020 | F6 | 20CA (019), 20URN (126) (RU2002126) |
| 2020 | F7 | Puerto Rico Seed Increase Purification |
| 2021 | F8 | 21CA_CN (003), 21URRN (010), 21DOP (008) |

In 15 head-to-head comparisons with checks across three years (2019-2021), the average yield of 'Addi Jo' was 7656 lb/A, compared to 7360 lb/A for Cheniere, 8428 lb/A for Jupiter, and 7949 lb/A for Mermentau. 'Addi Jo' averaged 103.8 cm in height in yield tests across Louisiana, which is approximately 1 cm taller than CL153, 3 cm taller than Mermentau, 4 cm taller than Cheniere, and 8 cm taller than Jupiter. 'Addi Jo' and Jupiter are both 83 days to 50% heading, which are 5 days later than Mermentau and 3 and 2 days later than Cheniere and CL153, respectively. The leaves, lemma, and palea of 'Addi Jo' are glabrous and the spikelet is straw-colored.

'Addi Jo' is the first high-amylose grain line developed for release in Louisiana. It contains an intermediate gelatinization temperature and is non-aromatic. This grain type is highly desirable for Latin American export markets, and for food processing inside or outside the United States. 'Addi Jo' contains the blast resistance gene Pita, which confers resistance to all documented races of blast disease in Louisiana; and the *Cercospora* resistance gene CRSP2.1, which confers broad-spectrum resistance. 'Addi Jo' is moderately susceptible to sheath blight and bacterial panicle blight, resistant to blast, and moderately resistant to *Cercospora* and false smut.

Variants observed and removed from increase fields of 'Addi Jo' primarily include taller and earlier maturing plants; or any combination of the following: pubescent, taller, shorter, later, earlier, short-, medium-, and intermediate-grain types, gold and black hull, and sterile panicle. The total numbers of variants were less than 1 per 10,000 plants.

Analysis of milled grains of 'Addi Jo' by standard means gave the following measurements: Apparent Amylose Percent=28.5%. Peak Viscosity=3045 cp. Trough Viscosity=2244 cp. Breakdown Viscosity=801 cp. Final Viscosity=4182 cp. Setback 2=1137 cp. Peak Time=6.4 min. Gelatinization temperature=83.55° C.

Evaluation of visual quality traits was conducted using the SeedCount reflectance image analysis system (SC6000R, Next Instruments Pty Ltd., Condell Park, NSW, Australia). Milled samples were ground into flour using a cyclone grinder (UDY Corporation) and filtered with a 1 mm screen. Gelatinization temperature was measured for the resulting rice flour with a Rapid-Visco Analyzer (RVA 4500 Perten Instruments), based on the Method 61-04.01 (American Association of Cereal Chemists, 2000). The amylose content of samples of rice flour was measured with an automated QuikChem 8500 Series 2 flow-injection analyzer system (QuikChem Method 20-244-00-1-A, Lachat Instrument, Loveland, CO). The amylose standard used was manufactured by Megazyme from potato starch (CAS Number 9005-82-7). The viscosity of samples of rice flour was evaluated with the RVA based on Method 61-02.01 (American Association of Cereal Chemists, 2000). The RVA parameters were determined by the various points on the viscosity curve, measured in centipoise (cP), corresponding to three stages: heated from 50° C. to 95° C., holding at 95° C. (holding), and cooling back to 50° C. The parameters determined were the following: pasting temperature, the temperature of the initial viscosity change; peak viscosity, the maximum viscosity during heating and holding; peak time, the time required to reach peak viscosity; trough viscosity, the minimum viscosity during cooling; final viscosity, the maximum viscosity after cooling; setback 2 viscosity, calculated as final viscosity minus peak viscosity; and breakdown viscosity, calculated as peak viscosity minus trough viscosity.

Variety Description Information

Rice cultivar 'Addi Jo' was observed to possess the following morphological and other characteristics, based on averages of tests conducted at multiple locations over several growing seasons; data for other varieties are shown for comparison:

TABLE B

| | Data Summary Table | | | | | | |
|---|---|---|---|---|---|---|---|
| | Performance | | | | | | |
| Trait | LA20-2126 | CHNR | CL153 | JPTR | MRMT | Number of Tests | Reference |
| Yield (lb/A) 2018 | 9504 | 8639 | 10050 | NA | NA | 1 | Table 1 |
| Yield (lb/A) 2019 | 5956 | 6061 | 7055 | 7164 | 6945 | 3 | Table 1 |
| Yield (lb/A) 2020 | 8255 | 7667 | 8629 | 8709 | 8443 | 5 | Table 1 |
| Yield (lb/A) 2021 | 7958 | 7698 | NA | 8771 | 8026 | 7 | Table 1 |
| Ratoon Yield (lb/A)* | 1830 | 1703 | 1050 | 1929 | 2371 | 4 | Table 2 |
| Whole (%)* | 60.6 | 63.4 | 60.7 | 63.3 | 62.9 | 6 | Table 3 |
| Total (%)* | 69.5 | 71.7 | 69.8 | 68.2 | 70.5 | 6 | Table 4 |
| Vigor* | 3.4 | 3.5 | 3.3 | 3.3 | 2.9 | 6 | Table 5 |
| Height (cm)* | 103.8 | 99.3 | 102.5 | 95.5 | 100.5 | 8 | Table 6 |
| Days to 50% Heading* | 82.7 | 80.4 | 81.0 | 83.6 | 78.8 | 7 | Table 7 |
| % Chalk* | 11.9 | 7.3 | 10.7 | 12.5 | 11.7 | 6 | Table 8 |
| Length-Milled (mm)* | 7.1 | 6.9 | 7.0 | 5.9 | 7.1 | 6 | Table 9 |
| Width-Milled (mm)* | 2.4 | 2.4 | 2.3 | 2.8 | 2.3 | 6 | Table 10 |
| L/W Ratio-Milled* | 3.0 | 2.9 | 3.1 | 2.1 | 3.1 | 6 | Table 11 |
| Whiteness-Milled* | 37.5 | 37.8 | 38.5 | 35.5 | 35.7 | 6 | Table 12 |
| Additional Trials | | | | | | | |
| 2021 Date of Planting 1-8 Yield | 7753 | 7765 | 8159 | NA | NA | 8 | Table 13 |
| 2021 Date of Planting 1-3 Ratoon Yield | 2864 | 2145 | 2494 | NA | NA | 3 | Table 14 |
| 2020-2021 URRN Yield | 9227 | 9005 | 9542 | 9227 | NA | 1 | Table 15 |
| Disease Data+ | | | | | | | |
| Sheath Blight | MS | S | S | MS | S | | |
| Blast | R | MS | MS | S | S | | |
| Bacterial Pan. Blight | MS | MS | MS | MR | MS | | |
| Narrow Brown Leaf Spot | MR | S | MS | R | MS | | |
| False Smut | MR | MR | MR | MR | MR | | |

*Summary traits are based on 2019 and 2020 data.
+Disease data taken from the LSU AgCenter's 2022 Rice Varieties and Management Tips for all varieties except LA20-2126.

TABLE 1

Average main crop yields (lb/A) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 9504 | 8639 | 10050 | NA | NA |
| 2019 | RYT-IOWA | 2409 | 2171 | 2750 | 2677 | 3587 |
| | RYT-LAKE ARTHUR | 2881 | 2650 | 5921 | 6292 | 6464 |
| | RYT-RRS | 7424 | 8695 | 9908 | 8631 | 9476 |
| | RYT-RRS-SOUTH | 8074 | 6884 | 6875 | 8321 | 6801 |
| | RYT-ST. JOSEPH | 8992 | 9904 | 9822 | 9898 | 8400 |
| | 2019 Average | 5956 | 6061 | 7055 | 7164 | 6945 |
| 2020 | CA-MAMOU | 9040 | 8114 | 9446 | 8721 | 8644 |
| | CA-MOWATA | 6201 | 5826 | 7358 | 7074 | 7871 |
| | CA-PALMETTO | 7992 | 7499 | 7495 | 8889 | 7589 |
| | CA-RRS | 10204 | 9515 | 10732 | 10627 | 9878 |
| | CA-RRS-SOUTH | 7841 | 7380 | 8115 | 8234 | 8231 |
| | 2020 Average | 8255 | 7667 | 8629 | 8709 | 8443 |
| 2021 | CA_CN_IOWA | 7421 | 7859 | NA | 8148 | 7732 |
| | CA_CN_LAKE ARTHUR | 9167 | 9392 | NA | 9884 | 9800 |
| | CA_CN_PALMETTO | 7235 | 5754 | NA | 7183 | 5984 |
| | CA_CN_RRS | 8469 | 7712 | NA | 8896 | 8609 |
| | CA_CN_RRS_SOUTH | 8163 | 8370 | NA | 9642 | 9161 |
| | CA_CN_ST. JOSEPH | 8108 | 8031 | NA | 9052 | 8466 |
| | CA_CN_WINNSBORO | 7143 | 6767 | NA | 8594 | 6431 |
| | 2021 Average | 7958 | 7698 | NA | 8771 | 8026 |

Notes:
RRS = Louisiana State University Rice Research Station (Crowley, LA)
Multiply lb/A by 1.121 to obtain kg/ha

TABLE 2

Average ratoon crop yields (lb/A) for LA20-2126, Cheniere, CL153, Jupiter and Mermentau at the H. Rouse Caffey Rice Research Station (2018, 2019, 2020, and 2021).

| YEAR | TEST | LA20-2126 | CHNR | CL153 | JPTR | MRMT |
|---|---|---|---|---|---|---|
| 2020 | CA-RRS | 1077 | 1246 | 1050 | 1323 | 2487 |
| 2021 | CA_CN_IOWA | 2072 | 1839 | NA | 2599 | 2155 |
|  | CA_CN_LAKE ARTHUR | 2298 | 1894 | NA | 2338 | 1808 |
|  | CA_CN_RRS | 3378 | 2748 | NA | 2668 | 2802 |
|  | 2021 Average | 2583 | 2160 | NA | 2535 | 2255 |

TABLE 3

Whole rice yield (%) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 64.9 | NA | 65.8 | NA | NA |
| 2019 | RYT-RRS | 60.2 | 66.7 | 65.1 | 64.9 | 66.7 |
|  | RYT-RRS-SOUTH | 60.6 | 61.4 | 58.0 | 61.8 | 62.0 |
|  | 2019 Average | 60.4 | 64.1 | 61.6 | 63.4 | 64.3 |
| 2020 | CA-MAMOU | 60.0 | 64.6 | 63.0 | 64.6 | 62.7 |
|  | CA-PALMETTO | 60.2 | 59.6 | 53.2 | 60.5 | 58.0 |
|  | CA-RRS | 62.7 | 64.0 | 64.4 | 64.9 | 62.6 |
|  | CA-RRS-SOUTH | 60.0 | 62.7 | 58.7 | 62.9 | 62.6 |
|  | 2020 Average | 60.7 | 62.7 | 59.8 | 63.2 | 61.5 |
| 2021 | CA_CN_LAKE ARTHUR | 59.9 | 65.5 | NA | 63.5 | 62.9 |
|  | CA_CN_RRS | 56.4 | 63.4 | NA | 59.8 | 60.9 |
|  | CA_CN_RRS_SOUTH | 61.8 | 65.7 | NA | 64.5 | 63.3 |
|  | CA_CN_ST. JOSEPH | 68.0 | 69.6 | NA | 61.4 | 67.0 |
|  | CA_CN_WINNSBORO | 60.9 | 55.1 | NA | 64.1 | 59.1 |
|  | 2021 Average | 61.4 | 63.9 | NA | 62.6 | 62.6 |

TABLE 4

Total rice yield (%) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 71.1 | NA | 71.5 | NA | NA |
| 2019 | RYT-RRS | 69.8 | 72.6 | 71.3 | 68.8 | 72.0 |
|  | RYT-RRS-SOUTH | 68.0 | 70.0 | 67.2 | 67.0 | 69.2 |
|  | 2019 Average | 68.9 | 71.3 | 69.2 | 67.9 | 70.6 |
| 2020 | CA-MAMOU | 69.5 | 72.1 | 70.6 | 69.3 | 70.8 |
|  | CA-PALMETTO | 68.7 | 70.3 | 68.0 | 66.4 | 67.8 |
|  | CA-RRS | 71.2 | 72.7 | 71.4 | 70.1 | 71.2 |
|  | CA-RRS-SOUTH | 71.0 | 73.2 | 71.6 | 68.0 | 71.8 |
|  | 2020 Average | 70.1 | 72.1 | 70.4 | 68.4 | 70.4 |
| 2021 | CA_CN_LAKE ARTHUR | 70.5 | 72.6 | NA | 67.4 | 70.1 |
|  | CA_CN_RRS | 66.5 | 70.2 | NA | 64.8 | 68.2 |
|  | CA_CN_RRS_SOUTH | 68.6 | 71.3 | NA | 68.8 | 69.4 |
|  | CA_CN_ST. JOSEPH | 72.3 | 73.9 | NA | 70.4 | 72.2 |
|  | CA_CN_WINNSBORO | 71.0 | 71.7 | NA | 71.3 | 70.7 |
|  | 2021 Average | 69.8 | 71.9 | NA | 68.5 | 70.1 |

TABLE 5

Seedling vigor for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 4.0 | 4.5 | 2.5 | NA | NA |
| 2019 | RYT-IOWA | 5.0 | 4.0 | 5.0 | 3.5 | 3.5 |

TABLE 5-continued

Seedling vigor for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| | RYT-RRS | 3.0 | 3.0 | 3.0 | 3.0 | 2.5 |
| | RYT-RRS-SOUTH | 2.5 | 2.5 | 2.5 | 3.0 | 2.0 |
| | 2019 Average | 3.5 | 3.2 | 3.5 | 3.2 | 2.7 |
| 2020 | CA-MAMOU | 3.0 | 5.0 | 3.3 | 3.3 | 3.3 |
| | CA-RRS | 3.7 | 3.3 | 3.0 | 3.7 | 3.0 |
| | CA-RRS-SOUTH | 3.0 | 3.3 | 2.7 | 3.3 | 3.0 |
| | 2020 Average | 3.2 | 3.9 | 3.0 | 3.4 | 3.1 |
| 2021 | CA_CN_IOWA | 3.0 | 3.3 | NA | 3.0 | 3.0 |
| | CA_CN_LAKE ARTHUR | 3.3 | 4.3 | NA | 4.0 | 3.0 |
| | CA_CN_RRS | 3.0 | 3.3 | NA | 3.0 | 2.7 |
| | CA_CN_RRS_SOUTH | 3.7 | 3.7 | NA | 3.7 | 3.3 |
| | 2021 Average | 3.3 | 3.7 | NA | 3.4 | 3.0 |

TABLE 6

Mean plant height (cm) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 95.5 | 87.0 | 90.0 | NA | NA |
| 2019 | RYT-IOWA | 98.5 | 92.0 | 97.5 | 91.5 | 99.0 |
| | RYT-RRS | 108.0 | 97.0 | 102.5 | 95.0 | 103.5 |
| | RYT-RRS-SOUTH | 105.5 | 93.0 | 109.5 | 96.0 | 102.0 |
| | 2019 Average | 104.0 | 94.0 | 103.2 | 94.2 | 101.5 |
| 2020 | CA-MAMOU | 103.0 | 113.3 | 105.3 | 97.7 | 105.0 |
| | CA-MOWATA | 106.0 | 105.5 | 103.5 | 90.5 | 102.5 |
| | CA-PALMETTO | 116.8 | 112.6 | 105.0 | 108.4 | 98.2 |
| | CA-RRS | 98.3 | 97.0 | 99.5 | 96.2 | 96.7 |
| | CA-RRS-SOUTH | 93.7 | 94.7 | 96.3 | 91.0 | 95.3 |
| | 2020 Average | 103.6 | 104.6 | 101.9 | 96.7 | 99.5 |
| 2021 | CA_CN_IOWA | 94.0 | 95.3 | NA | 89.3 | 92.7 |
| | CA_CN_LAKE ARTHUR | 94.0 | 92.0 | NA | 94.3 | 93.0 |
| | CA_CN_PALMETTO | 104.1 | 101.6 | NA | 96.5 | 99.1 |
| | CA_CN_RRS | 105.3 | 100.7 | NA | 105.7 | 98.7 |
| | CA_CN_RRS_SOUTH | 102.0 | 103.3 | NA | 104.3 | 108.0 |
| | CA_CN_ST. JOSEPH | 96.3 | 103.8 | NA | 101.7 | 100.3 |
| | 2021 Average | 99.3 | 99.4 | NA | 98.6 | 98.6 |

TABLE 7

Mean number of days to 50% heading for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 75.0 | 73.0 | 71.0 | NA | NA |
| 2019 | RYT-IOWA | 81.0 | 79.0 | 79.0 | 80.0 | 75.0 |
| | CA-RRS | 90.0 | 84.5 | 86.5 | 87.5 | 82.0 |
| | CA-RRS-SOUTH | 74.5 | 69.0 | 70.0 | 72.0 | 65.5 |
| | 2019 Average | 81.8 | 77.5 | 78.5 | 79.8 | 74.2 |
| 2020 | CA-MAMOU | 84.3 | 84.3 | 81.3 | 87.0 | 82.3 |
| | CA-PALMETTO | 80.7 | 79.0 | 84.3 | 84.3 | 83.7 |
| | CA-RRS | 88.2 | 87.8 | 87.5 | 91.5 | 86.2 |
| | CA-RRS-SOUTH | 80.3 | 79.0 | 78.7 | 82.7 | 77.0 |
| | 2020 Average | 83.4 | 82.5 | 83.0 | 86.4 | 82.3 |
| 2021 | CA_CN_IOWA | 85.0 | 87.0 | NA | 88.0 | 83.3 |
| | CA_CN_LAKE ARTHUR | 89.0 | 91.0 | NA | 97.3 | 87.7 |
| | CA_CN_RRS | 87.3 | 84.3 | NA | 88.0 | 80.7 |
| | CA_CN_RRS_SOUTH | 82.7 | 78.3 | NA | 81.3 | 75.7 |
| | 2021 Average | 86.0 | 85.2 | NA | 88.7 | 81.8 |

TABLE 8

Percent Chalk for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 11.4 | NA | 11.9 | NA | NA |
| 2019 | RYT-RRS | 11.2 | 11.0 | 11.5 | 11.2 | 14.3 |
|  | RYT-RRS-SOUTH | 13.1 | 3.4 | 7.9 | 7.5 | 8.2 |
|  | 2019 Average | 12.2 | 7.2 | 9.7 | 9.3 | 11.3 |
| 2020 | CA-MAMOU | 10.8 | 6.8 | 11.8 | 11.8 | 13.6 |
|  | CA-PALMETTO | 8.3 | 6.2 | 6.7 | 18.1 | 8.2 |
|  | CA-RRS | 16.5 | 9.8 | 17.1 | 17.1 | 13.7 |
|  | CA-RRS-SOUTH | 10.9 | 6.8 | 11.1 | 15.9 | 13.1 |
|  | 2020 Average | 11.6 | 7.4 | 11.7 | 15.7 | 12.1 |
| 2021 | CA_CN_LAKE ARTHUR | 15.6 | 9.0 | NA | 22.7 | 15.5 |
|  | CA_CN_RRS | 14.0 | 6.9 | NA | 18.4 | 17.5 |
|  | CA_CN_RRS_SOUTH | 16.9 | 7.2 | NA | 19.5 | 15.1 |
|  | CA_CN_ST. JOSEPH | 6.7 | 6.8 | NA | 8.6 | 12.6 |
|  | CA_CN_WINNSBORO | 12.3 | 8.6 | NA | 16.2 | 16.3 |
|  | 2021 Average | 13.1 | 7.7 | NA | 17.1 | 15.4 |

TABLE 9

Average milled grain length (mm) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 7.3 | NA | 7.2 | NA | NA |
| 2019 | RYT-RRS | 7.1 | 7.0 | 7.0 | 6.0 | 7.2 |
|  | RYT-RRS-SOUTH | 7.1 | 6.9 | 6.9 | 5.8 | 7.3 |
|  | 2019 Average | 7.1 | 6.9 | 7.0 | 5.9 | 7.2 |
| 2020 | CA-MAMOU | 7.1 | 7.0 | 7.0 | 5.9 | 6.9 |
|  | CA-PALMETTO | 7.0 | 6.8 | 6.9 | 5.7 | 6.7 |
|  | CA-RRS | 7.1 | 6.8 | 6.9 | 5.8 | 6.9 |
|  | CA-RRS-SOUTH | 7.2 | 7.1 | 7.1 | 6.0 | 7.1 |
|  | 2020 Average | 7.1 | 6.9 | 6.9 | 5.9 | 6.9 |
| 2021 | CA_CN_LAKE ARTHUR | 6.9 | 6.9 | NA | 5.9 | 6.8 |
|  | CA_CN_RRS | 6.9 | 6.9 | NA | 5.8 | 6.7 |
|  | CA_CN_RRS_SOUTH | 7.0 | 6.9 | NA | 5.8 | 6.8 |
|  | CA_CN_ST. JOSEPH | 7.2 | 7.0 | NA | 5.9 | 6.9 |
|  | CA_CN_WINNSBORO | 7.1 | 6.9 | NA | 5.9 | 6.8 |
|  | 2021 Average | 7.0 | 6.9 | NA | 5.9 | 6.8 |

TABLE 10

Average milled grain width (mm) for LA20-2126, Cheniere, CL153, Jupiter, and Mermentau across several trials at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 2.4 | NA | 2.3 | NA | NA |
| 2019 | RYT-RRS | 2.4 | 2.4 | 2.3 | 2.9 | 2.3 |
|  | RYT-RRS-SOUTH | 2.4 | 2.3 | 2.2 | 2.8 | 2.3 |
|  | 2019 Average | 2.4 | 2.3 | 2.2 | 2.8 | 2.3 |
| 2020 | CA-MAMOU | 2.4 | 2.3 | 2.3 | 2.8 | 2.2 |
|  | CA-PALMETTO | 2.5 | 2.4 | 2.4 | 2.9 | 2.3 |
|  | CA-RRS | 2.4 | 2.4 | 2.3 | 2.8 | 2.3 |
|  | CA-RRS-SOUTH | 2.4 | 2.4 | 2.3 | 2.8 | 2.3 |
|  | 2020 Average | 2.4 | 2.4 | 2.3 | 2.8 | 2.3 |
| 2021 | CA_CN_LAKE ARTHUR | 2.3 | 2.3 | NA | 2.7 | 2.2 |
|  | CA_CN_RRS | 2.4 | 2.4 | NA | 2.8 | 2.3 |
|  | CA_CN_RRS_SOUTH | 2.3 | 2.3 | NA | 2.7 | 2.2 |
|  | CA_CN_ST. JOSEPH | 2.4 | 2.4 | NA | 2.9 | 2.3 |
|  | CA_CN_WINNSBORO | 2.4 | 2.4 | NA | 2.8 | 2.3 |
|  | 2021 Average | 2.4 | 2.3 | NA | 2.8 | 2.3 |

TABLE 11

Average milled grain length-width ratio for LA20-2126, Cheniere,
CL153, Jupiter, and Mermentau across several trials at
multiple locations (2018, 2019, 2020, and 2021).

| YEAR | TEST | LA20-2126 | CHNR | CL153 | JPTR | MRMT |
|---|---|---|---|---|---|---|
| 2018 | PYL | 3.0 | NA | 3.1 | NA | NA |
| 2019 | RYT-RRS | 3.0 | 2.9 | 3.1 | 2.1 | 3.1 |
|  | RYT-RRS-SOUTH | 3.0 | 3.0 | 3.2 | 2.1 | 3.2 |
|  | 2019 Average | 3.0 | 3.0 | 3.1 | 2.1 | 3.1 |
| 2020 | CA-MAMOU | 3.0 | 3.0 | 3.1 | 2.1 | 3.1 |
|  | CA-PALMETTO | 2.8 | 2.8 | 2.9 | 2.0 | 3.0 |
|  | CA-RRS | 3.0 | 2.9 | 3.0 | 2.1 | 3.0 |
|  | CA-RRS-SOUTH | 3.0 | 3.0 | 3.1 | 2.1 | 3.1 |
|  | 2020 Average | 3.0 | 2.9 | 3.0 | 2.1 | 3.1 |
| 2021 | CA_CN_LAKE ARTHUR | 3.0 | 3.0 | NA | 2.2 | 3.1 |
|  | CA_CN_RRS | 2.9 | 2.9 | NA | 2.1 | 2.9 |
|  | CA_CN_RRS_SOUTH | 3.0 | 3.0 | NA | 2.1 | 3.0 |
|  | CA_CN_ST. JOSEPH | 3.0 | 3.0 | NA | 2.0 | 3.0 |
|  | CA_CN_WINNSBORO | 2.9 | 2.9 | NA | 2.1 | 2.9 |
|  | 2021 Average | 3.0 | 3.0 | NA | 2.1 | 3.0 |

TABLE 12

Average milled grain whiteness for LA20-2126, Cheniere,
CL153, Jupiter, and Mermentau across several trials
at multiple locations (2018, 2019, 2020, and 2021).

| YEAR | TEST | LA20-2126 | CHNR | CL153 | JPTR | MRMT |
|---|---|---|---|---|---|---|
| 2018 | PYL | 42.3 | NA | 44.9 | NA | NA |
| 2019 | RYT-RRS | 38.9 | 39.7 | 39.1 | 37.5 | 38.5 |
|  | RYT-RRS-SOUTH | 33.0 | 33.7 | 32.4 | 29.1 | 33.2 |
|  | 2019 Average | 35.9 | 36.7 | 35.7 | 33.3 | 35.8 |
| 2020 | CA-MAMOU | 37.6 | 38.8 | 40.4 | 34.7 | 35.3 |
|  | CA-PALMETTO | 38.8 | 40.2 | 41.2 | 38.1 | 36.5 |
|  | CA-RRS | 38.2 | 37.0 | 40.0 | 36.5 | 33.7 |
|  | CA-RRS-SOUTH | 42.0 | 39.6 | 43.7 | 41.5 | 36.7 |
|  | 2020 Average | 39.2 | 38.9 | 41.3 | 37.7 | 35.5 |
| 2021 | CA_CN_LAKE ARTHUR | 39.6 | 39.8 | NA | 39.3 | 37.9 |
|  | CA_CN_RRS | 38.3 | 38.1 | NA | 35.8 | 34.4 |
|  | CA_CN_RRS_SOUTH | 39.4 | 37.3 | NA | 38.0 | 34.6 |
|  | CA_CN_ST. JOSEPH | 39.5 | 39.7 | NA | 37.0 | 36.1 |
|  | CA_CN WINNSBORO | 36.9 | 35.1 | NA | 34.7 | 32.5 |
|  | 2021 Average | 38.7 | 38.0 | NA | 36.9 | 35.1 |

TABLE 13

Results of 2021 Date of Planting (DOP) Trial.

| Variety | Herbicide Type | Grain Type | Days to 50% Heading | Height (in) | Milling % (Whole/Total) | Chalk (%) | Grain Length (mm) | Lodging | DOP 1-DOP 3 Avg. |
|---|---|---|---|---|---|---|---|---|---|
| Cheniere | CONV | Long | 76 | 38 | 67/72 | 6.8 | 7.0 | R | 10,247 |
| CL153 | CL | Long | 75 | 40 | 65/70 | 8.5 | 7.0 | MR | 10,464 |
| CLL15 | CL | Long | 74 | 38 | 63/69 | 12.4 | 7.0 | MR | 10,355 |
| CLL17 | CL | Long | 72 | 40 | 63/69 | 11.2 | 6.7 | MS | 11,148 |
| DG263L | CONV | Long | 72 | 39 | 61/68 | 13.1 | 6.5 | MR | 11,559 |
| LA19-2026 | CL | Long | 71 | 38 | 64/70 | 15.6 | 7.0 | MR | 11,005 |
| LA19-2034 | CL | Long | 71 | 39 | 65/71 | 18.0 | 6.9 | MR | 11,300 |
| LA19-2207 | CONV | Long | 74 | 39 | 66/72 | 9.9 | 7.0 | MR | 10,617 |
| LA19-2212 | CONV | Long | 68 | 39 | 66/71 | 12.5 | 7.0 | MR | 10,943 |
| LA20-2126 | CONV | Long | 78 | 38 | 65/70 | 9.0 | 7.0 | MR | 10,312 |

TABLE 13-continued

Results of 2021 Date of Planting (DOP) Trial.

| | | | | | | | | | |
|---|---|---|---|---|---|---|---|---|---|
| LA20-2150 | CONV | Long | 75 | 41 | 64/71 | 12.8 | 7.1 | MR | 10,185 |
| PVL02 | PV | Long | 71 | 45 | 68/72 | 9.9 | 6.6 | S | 9,827 |
| PVL03 | PV | Long | 74 | 40 | 63/70 | 9.6 | 7.0 | MR | 10,208 |

| Variety | DOP 1 2/26 | DOP 2 3/12 | DOP 3 4/5 | DOP 4 4/22 | DOP 5 4/28 | DOP 6 5/26 | DOP 7 6/11 | DOP 8 6/18 | DOP 1-DOP 8 Avg. | DOP 1-DOP 3 Avg. |
|---|---|---|---|---|---|---|---|---|---|---|
| Cheniere | 10,382 | 10,641 | 9,718 | 7,910 | 7,716 | 5,480 | 4,974 | 5,296 | 7,765 | 10,247 |
| CL153 | 10,304 | 10,851 | 10,237 | 7,808 | 7,711 | 6,161 | 6,423 | 5,775 | 8,159 | 10,464 |
| CLL15 | 10,333 | 10,587 | 10,144 | 6,784 | 7,312 | 7,024 | 5,931 | 6,374 | 8,061 | 10,355 |
| CLL17 | 10,460 | 11,758 | 11,227 | 8,735 | 8,772 | 7,743 | 7,551 | 8,098 | 9,293 | 11,148 |
| DG263L | 9,914 | 12,967 | 11,797 | 10,247 | 9,862 | 7,950 | 7,567 | 6,858 | 9,645 | 11,559 |
| LA19-2026 | 11,195 | 10,906 | 10,915 | 8,941 | 8,877 | 7,278 | 7,648 | 8,297 | 9,257 | 11,005 |
| LA19-2034 | 10,636 | 12,008 | 11,257 | 9,138 | 9,005 | 7,787 | 7,715 | 8,313 | 9,482 | 11,300 |
| LA19-2207 | 10,783 | 10,576 | 10,493 | 7,579 | 8,410 | 6,154 | 6,388 | 7,226 | 8,451 | 10,617 |
| LA19-2212 | 10,605 | 11,215 | 11,008 | 9,126 | 8,900 | 7,872 | 6,880 | 7,733 | 9,167 | 10,943 |
| LA20-2126 | 10,843 | 10,793 | 9,300 | 8,025 | 7,856 | 5,067 | 5,043 | 5,100 | 7,753 | 10,312 |
| LA20-2150 | 10,380 | 10,763 | 9,411 | 8,207 | 8,025 | 6,434 | 6,534 | 6,618 | 8,297 | 10,185 |
| PVL02 | 9,561 | 10,790 | 9,130 | 7,486 | 7,206 | 7,339 | 6,216 | 7,450 | 8,147 | 9,827 |
| PVL03 | 10,606 | 10,617 | 9,400 | 7,255 | 7,443 | 6,881 | 5,821 | 6,418 | 8,055 | 10,208 |

Table 13 Abbreviations: R = resistant, MR = moderately resistant, MS = moderately susceptible, S = susceptible.
Height: Height maturity in inches from soil line to extended panicle.
Chalk: Total percentage area of grain with chalk as determined by SeedCount image analyzer.
Lodging: Comparative estimate of resistance to lodging. Most varieties rated as resistant can lodge, especially under excessive levels of nitrogen.
Grain Traits: Average from DOP 1-DOP 4.
DOP 1-DOP 3 Average represents plantings in recommended planting window.

TABLE 14

Results of 2021 Date of Planting (DOP) Trial Ratoon Yield.

| Variety | Herbicide Type | Grain Type | DOP 1 11/2 | DOP 2 11/2 | DOP 3 11/9 | DOP 1-DOP 3 Avg. |
|---|---|---|---|---|---|---|
| Cheniere | CONV | Long | 2124 | 2262 | 2051 | 2145 |
| CL153 | CL | Long | 2450 | 2427 | 2606 | 2494 |
| CLL15 | CL | Long | 2328 | 2724 | 2779 | 2610 |
| CLL17 | CL | Long | 2675 | 2432 | 2772 | 2627 |
| DG263L | CONV | Long | 1234 | 2245 | 1847 | 1774 |
| LA19-2026 | CL | Long | 2510 | 2699 | 2935 | 2715 |
| LA19-2034 | CL | Long | 2352 | 2601 | 2496 | 2483 |
| LA19-2207 | CONV | Long | 3113 | 3024 | 2730 | 2956 |
| LA19-2212 | CONV | Long | 2588 | 2860 | 2760 | 2736 |
| LA20-2126 | CONV | Long | 3077 | 2791 | 2724 | 2864 |
| LA20-2150 | CONV | Long | 2775 | 2872 | 2361 | 2669 |
| PVL02 | PV | Long | 3097 | 2953 | 2909 | 2987 |
| PVL03 | PV | Long | 2886 | 2954 | 3047 | 2962 |

DOP 1-DOP 3 Average represents plantings in recommended planting window.

TABLE 15

Results from testing in the Uniform Regional Rice Nursery (2020 and 2021).

| Year | Variety | Herbicide Type | Grain Type | Days to 50% Heading | Seedling Vigor | Height (cm) | Milling % (Whole/Total) | Chalk (%) |
|---|---|---|---|---|---|---|---|---|
| 2020 | Cheniere | CONV | Long | 96 | 3.0 | 89.7 | 62.4/71.8 | 10.9 |
| | CL153 | CL | Long | 97 | 3.0 | 96.3 | 63.0/70.3 | 18.0 |
| | Jupiter | CONV | Med | 98 | 5.0 | 97.7 | 61.2/69.1 | 23.2 |
| | PVL03 | PV | Long | 91 | 3.0 | 97.3 | 62.8/71.6 | 17.6 |
| | Thad | CONV | Long | 89 | 5.0 | 99.0 | 58.8/70.5 | 14.3 |
| | LA19-2212 | CONV | Long | 89 | 3.0 | 99.3 | 61.4/70.2 | 14.6 |
| | LA20-2126 | CONV | Long | 93 | 3.0 | 95.0 | 60.1/70.7 | 20.7 |
| 2021 | Cheniere | CONV | Long | 93 | 3.3 | 93.0 | 73.1/76.4 | 12.2 |
| | CL153 | CL | Long | 92 | 4.0 | 100.0 | 67.0/70.7 | 11.3 |
| | Jupiter | CONV | Med | 95 | 4.0 | 88.0 | 67.4/70.8 | 28.5 |
| | PVL03 | PV | Long | 89 | 4.0 | 103.0 | 67.9/73.9 | 11.0 |
| | Thad | CONV | Long | 87 | 3.5 | 95.5 | 57.4/70.5 | 9.0 |
| | LA19-2212 | CONV | Long | 86 | 4.0 | 87.3 | 65.9/71.0 | 15.6 |
| | LA20-2126 | CONV | Long | 89 | 3.7 | 94.3 | 64.1/70.2 | 10.9 |

TABLE 15-continued

Results from testing in the Uniform Regional Rice Nursery (2020 and 2021).

| | | | | | | | | |
|---|---|---|---|---|---|---|---|---|
| 2020- | Cheniere | CONV | Long | 95 | 3.2 | 91.4 | 67.8/74.1 | 11.5 |
| 2021 | CL153 | CL | Long | 95 | 3.5 | 98.2 | 65.0/70.5 | 14.7 |
| Avg. | Jupiter | CONV | Med | 97 | 4.5 | 92.9 | 64.3/70.0 | 25.9 |
| | PVL03 | PV | Long | 90 | 3.5 | 100.2 | 65.4/72.8 | 14.3 |
| | Thad | CONV | Long | 88 | 4.3 | 97.3 | 58.1/70.5 | 11.6 |
| | LA19-2212 | CONV | Long | 88 | 3.5 | 93.3 | 63.7/70.6 | 15.1 |
| | LA20-2126 | CONV | Long | 91 | 3.4 | 94.7 | 62.1/70.5 | 15.8 |

| Year | Variety | Grain Length (mm) | Grain Width (mm) | L/W Ratio | Whiteness | Yield (lb) | Ratoon (lb) |
|---|---|---|---|---|---|---|---|
| 2020 | Cheniere | 6.8 | 2.4 | 2.8 | 36.2 | 9020 | 1505 |
| | CL153 | 6.8 | 2.3 | 2.9 | 38.2 | 9843 | 1345 |
| | Jupiter | 5.7 | 2.9 | 2.0 | 35.5 | 8861 | 953 |
| | PVL03 | 7.0 | 2.4 | 2.9 | 37.1 | 9499 | 1666 |
| | Thad | 6.8 | 2.5 | 2.7 | 39.6 | 8534 | 2746 |
| | LA19-2212 | 6.9 | 2.5 | 2.8 | 33.3 | 9449 | 1580 |
| | LA20-2126 | 7.0 | 2.4 | 2.9 | 36.2 | 10018 | 880 |
| 2021 | Cheniere | 7.0 | 2.3 | 3.0 | 34.8 | 8990 | 2172 |
| | CL153 | 6.9 | 2.3 | 3.1 | 45.0 | 9241 | 2711 |
| | Jupiter | 5.8 | 2.8 | 2.1 | 36.0 | 7959 | 1629 |
| | PVL03 | 7.2 | 2.3 | 3.1 | 36.9 | 8867 | 3130 |
| | Thad | 6.7 | 2.5 | 2.7 | 44.2 | 8164 | 2995 |
| | LA19-2212 | 7.0 | 2.3 | 3.0 | 41.6 | 8441 | 2808 |
| | LA20-2126 | 6.9 | 2.3 | 3.0 | 43.7 | 8435 | 2982 |
| 2020- | Cheniere | 6.9 | 2.4 | 2.9 | 35.5 | 9005 | 1839 |
| 2021 | CL153 | 6.9 | 2.3 | 3.0 | 41.6 | 9542 | 2028 |
| Avg. | Jupiter | 5.7 | 2.8 | 2.0 | 35.7 | 8410 | 1291 |
| | PVL03 | 7.1 | 2.3 | 3.0 | 37.0 | 9183 | 2398 |
| | Thad | 6.8 | 2.5 | 2.7 | 41.9 | 8349 | 2871 |
| | LA19-2212 | 7.0 | 2.4 | 2.9 | 37.5 | 8945 | 2194 |
| | LA20-2126 | 6.9 | 2.3 | 3.0 | 39.9 | 9227 | 1931 |

TABLE 16

Disease ratings for the 2021 Uniform Regional Rice Nursery.

| | Pest Name and Rating Date | | |
|---|---|---|---|
| Variety | Sheath Blight Aug. 12, 2021 | Blast Sep. 19, 2021 | False Smut Sep. 19, 2021 |
| Cheniere | 2.0 | 1.3 | 0.3 |
| CL153 | 1.6 | 1.3 | 0.2 |
| CLL17 | 2.5 | 2.0 | 0.3 |
| Jupiter | 3.5 | 0.6 | 1.4 |
| LA19-2212 | 2.4 | 1.9 | 1.1 |
| LA20-2126 | 2.6 | 0.2 | 0.5 |

Disease ratings are based on a scale of 0-9; 0 = no disease.

TABLE 17

Disease ratings for the 2021 Commercial Advanced Conventional trial at the H. Rouse Caffey Rice Research Station.

| | Pest Name and Rating Date | | |
|---|---|---|---|
| Variety | Sheath Blight Aug. 12, 2021 | Blast Sep. 19, 2021 | False Smut Sep. 19, 2021 |
| Cheniere | 3.7 | 2.6 | 0.2 |
| CL153 | 4.7 | 0.4 | 0.6 |
| CLL17 | 4.7 | 0.1 | 0.1 |
| Jupiter | 1.7 | 1.0 | 0 |
| LA19-2212 | 5 | 1.9 | 0.2 |
| LA20-2126 | 2.3 | 0.1 | 0.4 |
| Mermentau | 3.7 | 2.6 | 0.2 |

Disease ratings are based on a scale of 0-9; 0 = no disease.

TABLE 18

Disease ratings for the 2021 High-Low Multi-Location trial at the H. Rouse Caffey Rice Research Station.

| | Pest Name and Rating Date | | |
|---|---|---|---|
| Variety | Sheath Blight Aug. 13, 2021 | Blast Sep. 20, 2021 | False Smut Sep. 20, 2021 |
| Cheniere | 3.0 | 0.4 | 0 |
| LA20-2126 | 1.7 | 0 | 0 |

Disease ratings are based on a scale of 0-9; 0 = no disease.

*Disease ratings are based on a scale of 0-9: The higher the number, the greater the disease symptoms.

This invention is also directed to methods for producing a rice plant by crossing a first parent rice plant with a second parent rice plant to produce an F1 hybrid, wherein the first or second rice plant (i.e., the male parent or the female parent) is a rice plant from the line 'Addi Jo.' Optionally, both the first and second parent rice plants may be from the cultivar 'Addi Jo.' Breeding methods that employ the cultivar 'Addi Jo' are also part of this invention, including crossing, selfing, backcrossing, hybrid breeding, crossing to populations, the other breeding methods discussed in this specification, and other breeding methods otherwise known to those of skill in the art. Any plants produced using cultivar 'Addi Jo' as a parent or ancestor by any of these breeding methods are within the scope of this invention. The other parents or other lines used in such breeding programs may be any of the wide number of rice varieties, cultivars, populations, experimental lines, and other sources of rice germplasm known to the art.

For example, this invention includes methods for producing a first-generation hybrid rice plant by crossing a first parent rice plant with a second parent rice plant, wherein either the first or second parent rice plant (i.e., either the male parent or the female parent) is 'Addi Jo.' Further, this invention is also directed to methods for producing a hybrid rice line derived from 'Addi Jo' by crossing 'Addi Jo' with a second rice plant, and growing the F1 progeny seed. The crossing and growing steps may be repeated any number of times. Breeding methods using the rice line 'Addi Jo' are considered part of this invention, not only backcrossing and hybrid production, but also selfing, crosses to populations, and other breeding methods known in the art.

Optionally, either of the parents in such a cross, 'Addi Jo' or the other parent, may be produced in male-sterile form, using techniques otherwise known in the art.

In one embodiment, a later-generation rice plant produced from cultivar 'Addi Jo' as a parent or ancestor exhibits tolerance to applications of one or more classes of herbicides. Classes of herbicides include, but are not limited to, acetohydroxyacid synthase (AHAS) inhibitors; bleaching herbicides such as hydroxyphenylpyruvate dioxygenase (HPPD) inhibitors or phytoene desaturase (PDS) inhibitors; enolpyruvyl shikimate 3-phosphate synthase (EPSPS) inhibitors such as glyphosate; glutamine synthetase (GS) inhibitors such as glufosinate; auxinic herbicides, e.g., dicamba; lipid biosynthesis inhibitors such as ACCase inhibitors; or oxynil (i.e. bromoxynil or ioxynil) herbicides; protoporphyrinogen-IX oxidase (PPO) inhibitors other than saflufenacil ("other PPO inhibitors") (e.g., acifluorfen, butafenacil, carfentrazone, flufenpyr-ethyl, fomesafen, flumiclorac, flumioxazin, lactofen, oxadiargyl, oxadiazon, oxyfluorfen, sulfentrazone); lipid biosynthesis inhibitors such as acetyl CoA carboxylase (ACCase) inhibitors; oxynil (i.e. bromoxynil orioxynil) herbicides; ACCase-inhibitor(s); saflufenacil(s); p-hydroxyphenylpyruvate dioxygenase (4-HPPD) inhibitors; amide(s), e.g., propanil; and the like. AHAS-inhibitor herbicides include, e.g., imidazolinone herbicides, one or more sulfonylurea (SU) herbicides selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, and combinations thereof. ACCase inhibitor herbicides include, e.g., "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden).

In some embodiments rice plants that are produced using cultivar 'Addi Jo' as a parent or ancestor may be tolerant to ACCase inhibitors, such as the "dims" (e.g., cycloxydim, sethoxydim, clethodim, or tepraloxydim), the "fops" (e.g., clodinafop, diclofop, fluazifop, haloxyfop, or quizalofop), and the "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, rice plants that are produced using cultivar 'Addi Jo' as a parent or ancestor may also be tolerant to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof.

Such tolerance traits may be expressed, e.g., as mutant acetohydroxyacid synthase large subunit (AHASL) proteins, mutant ACCase proteins, mutant EPSPS proteins, or mutant glutamine synthetase proteins; or as a mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) protein having herbicide-degrading activity.

The rice plants hereof can also optionally be "stacked" with traits including, but not limited to, pesticidal traits such as Bt Cry and other proteins having pesticidal activity toward coleopteran, lepidopteran, nematode, or other pests; nutritional or nutraceutical traits such as modified oil content or oil profile traits, high protein or high amino acid concentration traits, and other trait types known in the art.

Furthermore, in another embodiment, rice plants are generated, e.g. by the use of recombinant DNA techniques, breeding, or otherwise by selection for desired traits, plants that are able to synthesize one or more proteins to improve their productivity, oil content, tolerance to drought, salinity or other growth-limiting environmental factors, or tolerance to arthropod, fungal, bacterial, or viral pests or pathogens of rice plants.

Furthermore, in other embodiments, rice plants are generated, e.g. by the use of recombinant DNA techniques, breeding, or otherwise by selection for desired traits to contain a modified amount of one or more substances or to contain one or more new substances, for example, to improve human or animal nutrition, e.g. health-promoting long-chain omega-3 fatty acids or unsaturated omega-9 fatty acids. (Cf Nexera® canola, Dow Agro Sciences, Canada).

Furthermore, in some embodiments, rice plants are generated, e.g. by the use of recombinant DNA techniques, breeding, or otherwise by selection for desired traits to contain increased amounts of vitamins, minerals, or improved profiles of nutraceutical compounds.

In one embodiment, rice plants are produced using cultivar 'Addi Jo' as a parent or higher-generation ancestor so that the new rice plants, relative to a wild-type rice plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), or 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, or 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, rice plants are produced using cultivar 'Addi Jo' as a parent or higher-generation ancestor so that the new rice plants, relative to a wild-type rice plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavins/tannins (such as the procyanidins comprising coumarin, proanthocyanidins, catechins, and anthocyanins); flavones; phytoestrogens such as coumestans; lignans; resveratrol; isoflavones e.g. genistein, daidzein, and glycitein; resorcyclic acid lactones; organosulfur compounds; phytosterols; terpenoids such as carnosol, rosmarinic acid, glycyrrhizin and saponins; chlorophyll; chlorphyllin, sugars, anthocyanins, and vanilla.

Optional active ingredients (A.I.s) for an agronomically-acceptable composition used in combination with 'Addi Jo' include, but are not limited to agronomically-acceptable fungicides such as strobilurins, e.g., pyraclostrobin, alone or in combination with, e.g., boscalid, epiconazole, metaconazole, tebuconazole, kresoxim-methyl, and the like; insecticides, nematicides, lepidoptericides, coleoptericides, or molluscicides (e.g., malathion, pyrethrins/pyrethrum, carbaryl, spinosad, permethrin, bifenthrin, and esfenvalerate).

In one embodiment, a saflufenacil A.I. is, e.g.: 2-chloro-5-[3,6-dihydro-3-methyl-2,6-dioxo-4-(trifluoromethyl)-1-(2H)-pyrimidinyl]-4-fluoro-N-[[methyl(1-methylethyl) amino]sulfonyl]benzamide (CAS: N'-{2-chloro-4-fluoro-5-[1,2,3,6-tetrahydro-3-methyl-2,6-dioxo-4-(trifluoromethyl) pyrimidin-1-yl] benzoyl}-N-isopropyl-N-methylsulfamide; Reg. No.: 372137-35-4); BAS-H800).

As used herein, unless context clearly indicates others, a reference to a named compound, (e.g., "saflufenacil") should be understood to include not only the specified compound itself, but also the compound's various salts and esters.

The compositions can also comprise auxiliary ingredients that are customary for the formulation of crop protection agents. Examples of auxiliaries customary for the formulation of crop protection agents include inert auxiliaries, solid carriers, surfactants (such as dispersants, protective colloids, emulsifiers, wetting agents, and tackifiers), organic and inorganic thickeners, penetrants (such as penetration-enhancing organosilicone surfactants or acidic sulfate chelates, e.g., CT-301™ available from Cheltec, Inc.), safeners, bactericides, antifreeze agents, antifoams, colorants, and adhesives. Formulations of the herbicide compositions useful herein can be prepared according to any method useful for that purpose in the art.

Examples of thickeners (i.e. compounds that modify flow properties, e.g. high viscosity in a state of rest and low viscosity in motion) include polysaccharides, such as xanthan gum (Kelzan® from Kelco), Rhodopol® 23 (Rhone Poulenc) or Veegum® (from R.T. Vanderbilt), and also various organic and inorganic sheet minerals, such as Attaclay® (from Engelhard).

Examples of antifoaming agents include silicone emulsions (for example, Silikon® SRE, Wacker or Rhodorsil® from Rhodia), long-chain alcohols, fatty acids, salts of fatty acids, organofluorine compounds, and mixtures thereof.

Bactericides can optionally be added for stabilizing the aqueous formulations. Examples include bactericides based on diclorophen and benzyl alcohol hemiformal (Proxel® from ICI, Acticide® RS from Thor Chemie, or Kathon® MK from Rohm & Haas), or isothiazolinone derivatives, such as alkylisothiazolinones and benzisothiazolinones (Acticide MBS from Thor Chemie).

Examples of antifreeze agents include ethylene glycol, propylene glycol, urea, and glycerol.

Examples of colorants include members of colorant classes such as the sparingly water-soluble pigments and the water-soluble dyes. Some examples include the dyes known under the names Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, and basic red 108.

Examples of adhesives include polyvinylpyrrolidone, polyvinyl acetate, polyvinyl alcohol, and tylose.

Suitable inert auxiliaries include, for example, the following: mineral oil fractions of medium to high boiling point, such as kerosene and diesel oil; coal tar oils; oils of vegetable or animal origin; aliphatic, cyclic and aromatic hydrocarbons, for example paraffins, tetrahydronaphthalene, alkylated naphthalenes and their derivatives, and alkylated benzenes and their derivatives; alcohols such as methanol, ethanol, propanol, butanol and cyclohexanol; ketones such as cyclohexanone; strongly polar solvents, for example amines such as N-methylpyrrolidone; and water; as well as mixtures thereof.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, and alkylated benzenes and their derivatives; alcohols such as methanol, ethanol, propanol, butanol and cyclohexanol; ketones such as cyclohexanone; strongly polar solvents, e.g. amines such as N-methylpyrrolidone; and water; as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, and magnesium oxide; ground synthetic materials; fertilizers such as ammonium sulfate, ammonium phosphate, ammonium nitrate, and ureas; and products of vegetable origin, such as cereal meal, tree bark meal, wood meal, nutshell meal, and cellulose powders; and mixtures thereof.

Suitable surfactants (e.g., adjuvants, wetting agents, tackifiers, dispersants, or emulsifiers) include the alkali metal salts, alkaline earth metal salts, and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG); and salts of fatty acids, alkyl- and alkylarylsulfonates, alkyl sulfates, lauryl ether sulfates and fatty alcohol sulfates; and salts of sulfated hexa-, hepta- and octadecanols; fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters; lignosulfite waste liquors; and proteins, denatured proteins, polysaccharides (e.g. methylcellulose), hydrophobically modified starches, polyvinyl alcohol (Mowiol types, Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone, and copolymers thereof, and mixtures thereof.

Powders, materials for broadcasting and dusts can be prepared by mixing or concomitant grinding of the A.I.s together with a solid carrier.

Granules, for example coated granules, impregnated granules and homogeneous granules, can be prepared by binding the A.I.s to solid carriers.

Aqueous-use forms can be prepared from emulsion concentrates, suspensions, pastes, wettable powders, or water-dispersible granules by adding water.

To prepare emulsions, pastes, or oil dispersions, the compositions can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, preferably suitable for dilution or dispersion with water.

It may be beneficial in some embodiments to apply the composition alone or in combination with other compositions, or in the form of a mixture with other crop protection agents, for example together with agents for controlling pests or phytopathogenic fungi or bacteria. Also of interest is miscibility with mineral salt solutions, which are employed for treating nutritional and trace element deficiencies. Other additives such as non-phytotoxic oils and oil concentrates can also be added.

Moreover, it may be useful to apply the composition in combination with safeners. Safeners are compounds that prevent or reduce herbicide-induced injury to useful plants without having a major effect on the intended herbicidal action of the herbicides. They can be applied either before sowing (e.g. on seed treatments, shoots, or seedlings) or in the pre-emergence application or post-emergence application of the crop plant. The safeners and the herbicides can be applied simultaneously or in succession.

Safeners include e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4), phosphorthiolates, and N-alkyl-O-phenyl-carbamates and their agriculturally-acceptable salts and their agriculturally-acceptable derivatives such amides, esters, and thioesters.

Those skilled in the art will recognize that some compounds used as herbicides, safeners, etc. are capable of forming geometric isomers, for example E/Z isomers, enantiomers, diastereomers, or other stereoisomers. In general, it is possible to use either pure isomers or mixtures of isomers. For example, some of the aryloxyphenoxy propionate herbicides are chiral, and some of them are commonly used in enantiomerically enriched or enantiopure form, e.g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P. Alternatively, the compounds may be used in racemic mixtures or other mixtures of geometric isomers.

In another aspect, herbicide(s) can be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed treatment formulations may additionally comprise binders, and optionally colorants as well.

Binders can be added to improve the adhesion of the active materials onto the seeds after treatment. Suitable binders include, e.g., block copolymers, EO/PO surfactants, polyvinylalcohols, polyvinylpyrrolidones, polyacrylates, polymethacrylates, polybutenes, polyisobutylenes, polystyrene, polyethyleneamines, polyethyleneamides, polyethyleneimines (e.g., Lupasol®, Polymin®), polyethers, polyurethanes, polyvinylacetate, tylose, and copolymers derived from these polymers.

The term "seed treatment" includes all suitable seed treatment techniques known in the art, including seed dressing, seed coating, seed dusting, seed soaking, and seed pelleting. Alternatively, or in addition, soil may be treated by applying a formulation containing the herbicide (e.g., a granular formulation), for example with a seed drill, with optionally one or more solid or liquid, agriculturally acceptable carriers, and optionally with one or more agriculturally acceptable surfactants.

The present invention also comprises seeds coated with or containing a seed treatment formulation comprising herbicide(s) or other compounds. The term "coated with or containing" generally signifies that the active ingredient is for the most part on the surface of the seed at the time of application, although a greater or lesser part of the ingredient may penetrate into the seed, depending on the method of application. When the seed is planted, it may absorb the active ingredient.

In some embodiments, the seed treatment is applied by spraying or dusting the seeds, or otherwise treating the seeds, before the seeds are sown. Alternatively, the seed treatment can comprise any one or more of the agriculturally acceptable herbicides, fungicides, insecticides, or nematicides, or combination thereof.

In still further aspects, loci, plants, plant parts, or seeds are treated with an agronomically acceptable composition that does not contain an A.I. For example, the treatment may comprise one or more agronomically-acceptable carriers, diluents, excipients, plant growth regulators, and the like; or an adjuvant, such as a surfactant, a spreader, a sticker, a penetrant, a drift-control agent, a crop oil, an emulsifier, a compatibility agent, or combinations thereof.

In other aspects, the present invention provides a product prepared from the rice plants of the invention, for example, brown rice (e.g., cargo rice), broken rice (e.g., chits, brewer's rice), polished rice (e.g., milled rice), rice hulls (e.g., husks, chaff), rice bran, rice pollards, rice mill feed, rice flour, rice oil, oiled rice bran, de-oiled rice bran, arrak, rice wine, poultry litter, and animal feed.

Further Embodiments of the Invention

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells that, upon growth and differentiation, produce a cultivar having essentially all of the physiological and morphological characteristics of 'Addi Jo.'

Techniques for transforming with and expressing desired structural genes and cultured cells are known in the art. Also, as known in the art, rice may be transformed and regenerated such that whole plants containing and expressing desired genes under regulatory control are obtained. General descriptions of plant expression vectors and reporter genes and transformation protocols can be found, for example, in Gruber et al., "Vectors for Plant Transformation, in Methods in Plant Molecular Biology & Biotechnology" in Glich et al. (Eds. pp. 89-119, CRC Press, 1993). For example, expression vectors and gene cassettes with the GUS reporter are available from Clone Tech Laboratories, Inc. (Palo Alto, Calif.), and expression vectors and gene cassettes with luciferase reporter are available from Promega Corp. (Madison, Wis.). General methods of culturing plant tissues are provided, for example, by Maki et al., "Procedures for Introducing Foreign DNA into Plants" in Methods in Plant Molecular Biology & Biotechnology, Glich et al., (Eds. pp. 67-88 CRC Press, 1993); by Phillips et al., "Cell-Tissue Culture and In-Vitro Manipulation" in Corn & Corn Improvement, 3rd Edition; and by Sprague et al., (Eds. pp. 345-387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of *Agrobacterium* vectors systems and methods for *Agrobacterium*-mediated gene transfer are provided by Gruber et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with biolistic device- or *Agrobacterium*-mediated transformation. Transformed plants obtained with the germplasm of 'Addi Jo' are intended to be within the scope of this invention.

The present invention also provides rice plants regenerated from a tissue culture of the 'Addi Jo' variety or hybrid plant. As is known in the art, tissue culture can be used for the in vitro regeneration of a rice plant. For example, see Chu, Q. R. et al. (1999) "Use of bridging parents with high anther culturability to improve plant regeneration and breeding value in rice," *Rice Biotechnology Quarterly*, 38:25-26; Chu, Q. R. et al., "A novel plant regeneration medium for rice anther culture of Southern U.S. crosses," *Rice Biotechnology Quarterly*, 35:15-16 (1998); Chu, Q. R. et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J. Breed.*, 33 (Supp. 2), 306-307 (1983). Thus, another aspect of this invention is to provide cells that, upon growth and differentiation, produce rice plants having all, or essentially all, of the physiological and morphological characteristics of variety 'Addi Jo.'

Unless context clearly indicates otherwise, references in the specification and claims to 'Addi Jo' should be understood also to include single gene conversions of 'Addi Jo' with a gene encoding a trait such as, for example, male sterility, herbicide resistance, resistance for bacterial, fungal, or viral disease, insect resistance, male fertility, enhanced nutritional quality, industrial usage, yield stability and yield enhancement.

Duncan et al., *Planta*, 165:322-332 (1985) reflects that 97% of the plants cultured that produced callus were capable of plant regeneration. Subsequent experiments with both inbreds and hybrids produced 91% regenerable callus that produced plants. In a further study, Songstad et al., Plant Cell Reports, 7:262-265 (1988) reported several media additions that enhanced regenerability of callus of two inbred lines. Other published reports also indicate that "nontraditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger et al., *Plant Cell Reports*, 6:345-347 (1987) reported somatic embryogenesis from the tissue cultures of corn leaf segments. These methods of obtaining plants are routinely used with a high rate of success.

Tissue culture of corn (maize) is described in European Patent Application No. 160,390. Corn tissue culture procedures, which may be adapted for use with rice, are also described in Green et al., "Plant Regeneration in Tissue Culture of Maize," *Maize for Biological Research* (Plant Molecular Biology Association, Charlottesville, Va., pp. 367-372, 1982) and in Duncan et al., "The Production of Callus Capable of Plant Regeneration from Immature Embryos of Numerous *Zea Mays* Genotypes," 165 Planta, 322:332 (1985). Thus, another aspect of this invention is to provide cells that, upon growth and differentiation, produce rice plants having all, or essentially all, of the physiological and morphological characteristics of hybrid rice line 'Addi Jo.' See T. P. Croughan et al., (Springer-Verlag, Berlin, 1991) Rice (*Oryza sativa*. L): Establishment of Callus Culture and the regeneration of Plants, in Biotechnology in Agriculture and Forestry (19-37).

With the advent of molecular biological techniques that allow the isolation and characterization of genes that encode specific protein products, it is now possible to routinely engineer plant genomes to incorporate and express foreign genes, or additional or modified versions of native, or endogenous, genes (perhaps driven by different promoters) in order to alter the traits of a plant in a specific manner. Such foreign, additional, and modified genes are herein referred to collectively as "transgenes." In recent years, several methods for producing transgenic plants have been developed, and the present invention, in particular embodiments, also relates to transformed versions of 'Addi Jo.'

An expression vector is constructed that will function in plant cells. Such a vector comprises a DNA coding sequence that is under the control of or is operatively linked to a regulatory element (e.g., a promoter). The expression vector may contain one or more such operably linked coding sequence/regulatory element combinations. The vector(s) may be in the form of a plasmid or virus, and can be used alone or in combination with other plasmids or viruses to provide transformed rice plants.

Expression Vectors

Expression vectors commonly include at least one genetic "marker," operably linked to a regulatory element (e.g., a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are known in the art, and include, for example, genes that code for enzymes that metabolically detoxify a selective chemical inhibitor such as an antibiotic or a herbicide, or genes that encode an altered target that is insensitive to such an inhibitor. Positive selection methods are also known in the art.

For example, a commonly used selectable marker gene for plant transformation is that for neomycin phosphotransferase II (nptII), isolated from transposon Tn5, whose expression confers resistance to kanamycin. See Fraley et al., Proc. Natl. Acad. Sci. U.S.A., 80:4803 (1983). Another commonly used selectable marker gene is the hygromycin phosphotransferase gene, which confers resistance to the antibiotic hygromycin. See Vanden Elzen et al., Plant Mol. Biol., 5:299 (1985).

Additional selectable marker genes of bacterial origin that confer resistance to one or more antibiotics include gentamycin acetyl transferase, streptomycin phosphotransferase, aminoglycoside-3'-adenyl transferase, and the bleomycin resistance determinant. Hayford et al., Plant Physiol., 86:1216 (1988), Jones et al., Mol. Gen. Genet., 210:86 (1987), Svab et al., Plant Mol. Biol., 14:197 (1990); Plant Mol. Biol., 7:171 (1986). Other selectable marker genes confer resistance to herbicides such as glyphosate, glufosinate, or broxynil. Comai et al., Nature, 317:741-744 (1985); Gordon-Kamm et al., Plant Cell, 2:603-618 (1990); and Stalker et al., Science, 242:419-423 (1988).

Selectable marker genes for plant transformation of non-bacterial origin include, for example, mouse dihydrofolate reductase, plant 5-enolpyruvylshikimate-3-phosphate synthase, and plant acetolactate synthase. Eichholtz et al., Somatic Cell Mol. Genet. 13:67 (1987); Shah et al., Science, 233:478 (1986); and Charest et al., Plant Cell Rep., 8:643 (1990).

Another class of marker genes for plant transformation employs screening of presumptively transformed plant cells, rather than selection for resistance to a toxic substance such as an antibiotic. These marker genes are particularly useful to quantify or visualize the spatial pattern of expression of a gene in specific tissues, and are frequently referred to as reporter genes because they may be fused to the target gene or regulatory sequence. Commonly used reporter genes include glucuronidase (GUS), galactosidase, luciferase, chloramphenicol, and acetyltransferase. See Jefferson, R. A., Plant Mol. Biol. Rep., 5:387 (1987); Teeri et al., EMBO J., 8:343 (1989); Koncz et al., Proc. Natl. Acad. Sci. U.S.A., 84:131 (1987); and DeBlock et al., EMBO J., 3:1681 (1984). Another approach to identifying relatively rare transformation events has been the use of a gene that encodes a dominant constitutive regulator of the *Zea mays* anthocyanin pigmentation pathway. Ludwig et al., Science, 247:449 (1990).

The Green Fluorescent Protein (GFP) gene has been used as a marker for gene expression in prokaryotic and eukaryotic cells. See Chalfie et al., Science, 263:802 (1994). GFP and mutants of GFP may be used as screenable markers.

Genes included in expression vectors are driven by a nucleotide sequence comprising a regulatory element, for example, a promoter. Many suitable promoters are known in the art, as are other regulatory elements that may be used either alone or in combination with promoters.

As used herein, "promoter" refers to a region of DNA upstream or downstream from the transcription initiation site, a region that is involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter primarily drives expression in certain cell types in one or more organs, for example, vascular cells in roots or leaves. An "inducible" promoter is a promoter that is under environmental control. Examples of environmental conditions that may induce transcription by inducible promoters include anaerobic conditions or the presence of light. Tissue-specific, tissue-preferred, cell type specific, and inducible promoters are examples of "non-constitutive" promoters. A "constitutive" promoter is a promoter that is generally active under most environmental conditions.

A. Inducible Promoters

An inducible promoter is operably linked to a gene for expression in rice. Optionally, the inducible promoter is operably linked to a nucleotide sequence encoding a signal sequence that is operably linked to a gene for expression in rice. With an inducible promoter the rate of transcription increases in response to an inducing agent.

Any suitable inducible promoter may be used in the present invention. See Ward et al., Plant Mol. Biol., 22:361-366 (1993). Examples include those from the ACEI system, which responds to copper, Meft et al., PNAS, 90:4567-4571 (1993); In2 gene from maize, which responds to benzenesulfonamide herbicide safeners, Hershey et al., Mol. Gen Genetics, 227:229-237 (1991); Gatz et al., Mol. Gen. Genetics, 243:32-38 (1994); and Tet repressor from Tn10, Gatz, Mol. Gen. Genetics, 227:229-237 (1991). A preferred inducible promoter is one that responds to an inducing agent to which plants do not normally respond, for example, the inducible promoter from a steroid hormone gene, the transcriptional activity of which is induced by a glucocorticosteroid hormone. See Schena et al., Proc. Natl. Acad. Sci., U.S.A. 88:0421 (1991).

B. Constitutive Promoters

A constitutive promoter is operably linked to a gene for expression in rice, or the constitutive promoter is operably linked to a nucleotide sequence encoding a signal sequence that is operably linked to a gene for expression in rice.

Constitutive promoters may also be used in the instant invention. Examples include promoters from plant viruses such as the 35S promoter from cauliflower mosaic virus, Odell et al., Nature, 313:810-812 (1985), and the promoters from the rice actin gene, McElroy et al., Plant Cell, 2:163-171 (1990); ubiquitin, Christensen et al., Plant Mol. Biol., 12:619-632 (1989) and Christensen et al., Plant Mol. Biol. 18:675-689 (1992); pEMU, Last et al., Theor. Appl. Genet., 81:581-588 (1991); MAS, Velten et al., EMBO J., 3:2723-2730 (1984); and maize H3 histone, Lepetit et al., Mol. Gen. Genetics, 231:276-285 (1992) and Atanassova et al., Plant Journal, 2 (3): 291-300 (1992). An ACCase or AHAS promoter, such as a rice ACCase or AHAS promoter, may be used as a constitutive promoter.

C. Tissue-Specific or Tissue-Preferred Promoters

A tissue-specific promoter is operably linked to a gene for expression in rice. Optionally, the tissue-specific promoter is operably linked to a nucleotide sequence encoding a signal sequence that is operably linked to a gene for expression in rice. Transformed plants produce the expression product of the transgene exclusively, or preferentially, in specific tissue(s).

Any tissue-specific or tissue-preferred promoter may be used in the instant invention. Examples of tissue-specific or tissue-preferred promoters include those from the phaseolin gene, Murai et al., Science, 23:476-482 (1983), and Sengupta-Gopalan et al., Proc. Natl. Acad. Sci. U.S.A., 82:3320-3324 (1985); a leaf-specific and light-induced promoter such as that from cab or rubisco, Simpson et al., EMBO J., 4(11):2723-2729 (1985) and Timko et al., Nature, 318:579-582 (1985); an anther-specific promoter such as that from LAT52, Twell et al., Mol. Gen. Genetics, 217:240-245 (1989); a pollen-specific promoter such as that from Zm13, Guerrero et al., Mol. Gen. Genetics, 244:161-168 (1993); or a microspore-preferred promoter such as that from apg, Twell et al., Sex. Plant Reprod., 6:217-224 (1993).

Signal Sequences for Targeting Proteins to Subcellular Compartments

Transport of protein or peptide molecules produced by transgenes to a subcellular compartment such as a chloroplast, vacuole, peroxisome, glyoxysome, cell wall, or mitochondrion, or for secretion into an apoplast, is accomplished by operably linking a nucleotide sequence encoding a signal sequence to the 5' or 3' end of a gene encoding the protein or peptide of interest. Targeting sequences at the 5' or 3' end of the structural gene may determine, during protein synthesis and processing, where the encoded protein is ultimately compartmentalized.

Many signal sequences are known in the art. See, for example, Becker et al., *Plant Mol. Biol.*, 20:49 (1992); Close, P. S., Master's Thesis, Iowa State University (1993); Knox, C. et al., "Structure and Organization of Two Divergent Alpha-Amylase Genes from Barley," *Plant Mol. Biol.*, 9:3-17 (1987); Lerner et al., *Plant Physiol.*, 91:124-129 (1989); Fontes et al., *Plant Cell*, 3:483-496 (1991); Matsuoka et al., *Proc. Natl. Acad. Sci.*, 88:834 (1991); Gould et al., *J. Cell. Biol.*, 108:1657 (1989); Creissen et al., *Plant J.*, 2:129 (1991); Kalderon et al., "A short amino acid sequence able to specify nuclear location," *Cell*, 39:499-509 (1984); and Steifel et al., "Expression of a maize cell wall hydroxyproline-rich glycoprotein gene in early leaf and root vascular differentiation," *Plant Cell*, 2:785-793 (1990).

Foreign Protein Genes and Agronomic Genes

Agronomically significant genes that may be transformed into rice plants in accordance with the present invention include, for example, the following:

1. Genes that Confer Resistance to Pests or Disease:
   A. Plant disease resistance genes. Plant defenses are often activated by specific interaction between the product of a disease resistance gene (R) in the plant and the product of a corresponding avirulence (Avr) gene in the pathogen. A plant may be transformed with a cloned resistance gene to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); and Mindrinos et al., *Cell* 78:1089 (1994) (*Arabidopsis* RSP2 gene for resistance to *Pseudomonas syringae*).
   B. A *Bacillus thuringiensis* protein, a derivative thereof, or a synthetic polypeptide modeled thereon. See, e.g., Geiser et al., *Gene* 48:109 (1986), disclosing the cloning and nucleotide sequence of a Bt-endotoxin gene. DNA molecules encoding endotoxin genes may be obtained from American Type Culture Collection, Manassas, Va., e.g., under ATCC Accession Nos. 40098, 67136, 31995, and 31998.
   C. A lectin. See, for example, Van Damme et al., *Plant Molec. Biol.* 24:25 (1994), disclosing the nucleotide sequences of several *Clivia miniata* mannose-binding lectin genes.
   D. A vitamin-binding protein such as avidin. See PCT Application US93/06487. This disclosure teaches the use of avidin and avidin homologues as larvicides against insect pests.
   E. An enzyme inhibitor, e.g., a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor 1); and Sumitani et al., *Biosci. Biotech. Biochem.* 57:1243 (1993) (nucleotide sequence of *Streptomyces nitrosporeus*-amylase inhibitor).
   F. An insect-specific hormone or pheromone such as an ecdysteroid and juvenile hormone, a variant thereof, a mimetic based thereon, or an antagonist or agonist thereof. See, e.g., Hammock et al., *Nature,* 344:458 (1990), disclosing baculovirus expression of cloned juvenile hormone esterase, an inactivator of juvenile hormone.
   G. An insect-specific peptide or neuropeptide that, upon expression, disrupts the physiology of the affected pest. See, e.g., Regan, *J. Biol. Chem.* 269:9 (1994) (expression cloning yields DNA coding for insect diuretic hormone receptor); and Pratt et al., *Biochem. Biophys. Res. Comm.,* 163:1243 (1989) (an allostatin in *Diploptera puntata*). See also U.S. Pat. No. 5,266,317 to Tomalski et al., disclosing genes encoding insect-specific, paralytic neurotoxins.
   H. An insect-specific venom produced in nature by a snake, a wasp, etc. For example, see Pang et al., *Gene,* 116:165 (1992), concerning heterologous expression in plants of a gene coding for a scorpion insectotoxic peptide.
   I. An enzyme responsible for hyperaccumulation of a monoterpene, a sesquiterpene, a steroid, hydroxamic acid, a phenylpropanoid derivative or another non-protein molecule with insecticidal activity.
   J. An enzyme involved in the modification, including post-translational modification, of a biologically active molecule; e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, either natural or synthetic. See PCT Application WO 9302197 to Scott et al., which discloses the nucleotide sequence of a callase gene. DNA molecules that contain chitinase-encoding sequences can be obtained, for example, from the American Type Culture Collection under Accession Nos. 39637 and 67152. See also Kramer et al., *Insect Biochem. Molec. Biol.* 23:691 (1993), which discloses the nucleotide sequence of a cDNA encoding tobacco hookworm chitinase; and Kawalleck et al., *Plant Molec. Biol.,* 21:673 (1993), which discloses the nucleotide sequence of the parsley ubi4-2 polyubiquitin gene.
   K. A molecule that stimulates signal transduction. See, e.g., Botella et al., *Plant Molec. Biol.,* 24:757 (1994), which discloses nucleotide sequences for mung bean calmodulin cDNA clones; and Griess et al., *Plant Physiol.,* 104:1467 (1994), which discloses the nucleotide sequence of a maize calmodulin cDNA clone.
   L. An antimicrobial or amphipathic peptide. See PCT Application WO 9516776 (disclosing peptide derivatives of Tachyplesin that inhibit fungal plant pathogens); and PCT Application WO 9518855 (disclosing synthetic antimicrobial peptides that confer disease resistance).
   M. A membrane permease, a channel former or a channel blocker. See, e.g., Jaynes et al., *Plant Sci.,* 89:43 (1993), which discloses heterologous expression of a cecropin lytic peptide analog to render transgenic tobacco plants resistant to *Pseudomonas solanacearum*.
   N. A viral-invasive protein or a complex toxin derived therefrom. For example, the accumulation of viral coat proteins in transformed plant cells induces resistance to viral infection or disease development caused by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. See Beachy et al., *Ann. Rev. Phytopathol.,* 28:451 (1990).

O. An insect-specific antibody or an immunotoxin derived therefrom. Thus, an antibody targeted to a critical metabolic function in the insect gut inactivates an affected enzyme, killing the insect. See Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

P. A virus-specific antibody. See, e.g., Tavladoraki et al., *Nature,* 366:469 (1993), showing protection of transgenic plants expressing recombinant antibody genes from virus attack.

Q. A developmental-arrest protein produced in nature by a pathogen or a parasite. For example, fungal endo-1,4-D-polygalacturonases facilitate fungal colonization and plant nutrient release by solubilizing plant cell wall homo-1,4-D-galacturonase. See Lamb et al., *Bio/Technology,* 10:1436 (1992). The cloning and characterization of a gene that encodes a bean endopolygalacturonase-inhibiting protein is described by Toubart et al., *Plant J.,* 2:367 (1992).

R. A developmental-arrest protein produced in nature by a plant. For example, Logemann et al., *Bio/Technology,* 10:305 (1992) reported that transgenic plants expressing the barley ribosome-inactivating gene have an increased resistance to fungal disease.

2. Genes that Confer Resistance to a Herbicide, for Example:
   A. A herbicide that inhibits the growing point or meristem, such as an imidazolinone or a sulfonylurea. Exemplary genes in this category code for mutant ALS and AHAS enzymes as described, for example, by Lee et al., *EMBO J.,* 7:1241 (1988); and Miki et al., *Theor. Appl. Genet.,* 80:449 (1990), respectively. See, additionally, U.S. Pat. Nos. 5,545, 822; 5,736,629; 5,773,703; 5,773,704; 5,952,553; 6,274,796; 6,943,280; 7,019,196; 7,345,221; 7,399, 905; 7,495,153; 7,754,947; 7,786,360; 8,841,525; 8,841,526; 8,946,528; 9,029,642; 9,090,904; and 9,220,220. Resistance to AHAS-acting herbicides may be through a mechanism other than a resistant AHAS enzyme. See, e.g., U.S. Pat. No. 5,545,822.
   B. Glyphosate: Resistance may be imparted by mutant 5-enolpyruvl-3-phosphikimate synthase (EPSP) and aroA genes. Other phosphono compounds such as glufosinate: Resistance may be imparted by phosphinothricin acetyl transferase, PAT, and *Streptomyces hygroscopicus* phosphinothricin-acetyl transferase, bar, genes. Pyridinoxy or phenoxy propionic acids and cyclohexones: Resistance may be imparted by ACCase inhibitor-encoding genes. See, e.g., U.S. Pat. No. 4,940,835 to Shah et al., which discloses the nucleotide sequence of a form of EPSP that confers glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application No. 0333033 to Kumada et al.; and U.S. Pat. No. 4,975,374 to Goodman et al., disclose nucleotide sequences of glutamine synthetase genes that confer resistance to herbicides such as L-phosphinothricin. The nucleotide sequence of a phosphinothricin-acetyl-transferase gene is provided in European Application No. 0242246 to Leemans et al. and DeGreef et al., *Bio/Technology,* 7:61 (1989), describing the production of transgenic plants that express chimeric bar genes coding for phosphinothricin acetyl transferase activity. Examples of genes conferring resistance to phenoxy propionic acids and cyclohexones, such as sethoxydim and haloxyfop, are the Acc1-S1, Acc1-S2, and Acc1-S3 genes described by Marshall et al., *Theor. Appl. Genet.,* 83:435 (1992).

C. A herbicide that inhibits photosynthesis, such as a triazine (psbA and gs+ genes) or a benzonitrile (nitrilase gene). Przibilla et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.,* 285:173 (1992).

3. Genes that Confer or Contribute to a Value-added Trait, such as:
   A. Modified fatty acid metabolism, for example, by transforming a plant with an antisense sequence to stearyl-ACP desaturase, to increase stearic acid content of the plant. See Knultzon et al., *Proc. Natl. Acad. Sci. U.S.A.* 89:2624 (1992).
   B. Decreased Phytate Content
      1) Introduction of a phytase-encoding gene would enhance breakdown of phytate, adding more free phosphate to the transformed plant. See, e.g., Van Hartingsveldt et al., *Gene,* 127:87 (1993), which discloses the nucleotide sequence of an *Aspergillus niger* phytase gene.
      2) A gene may be introduced to reduce phytate content. For example, this may be accomplished by cloning, and then reintroducing DNA associated with an allele that is responsible for maize mutants characterized by low levels of phytic acid, or a homologous or analogous mutation in rice may be used. See Raboy et al., *Maydica,* 35:383 (1990).
   C. Carbohydrate composition may be modified, for example, by transforming plants with a gene coding for an enzyme that alters the branching pattern of starch. See Shiroza et al., *J. Bacteol.,* 170:810 (1988) (nucleotide sequence of *Streptococcus* mutant fructosyltransferase gene); Steinmetz et al., *Mol. Gen. Genet.,* 20:220 (1985) (nucleotide sequence of *Bacillus subtilis* levansucrase gene); Pen et al., *Bio/Technology,* 10:292 (1992) (production of transgenic plants that express *Bacillus licheniformis* amylase); Elliot et al., *Plant Molec. Biol.,* 21:515 (1993) (nucleotide sequences of tomato invertase genes); Søgaard et al., *J. Biol. Chem.,* 268:22480 (1993) (site-directed mutagenesis of barley amylase gene); and Fisher et al., *Plant Physiol.,* 102:1045 (1993) (maize endosperm starch branching enzyme II).

Methods for Rice Transformation

Numerous methods for plant transformation are known in the art, including both biological and physical transformation protocols. See, e.g., Miki, et al., "Procedures for Introducing Foreign DNA into Plants" in *Methods in Plant Molecular Biology and Biotechnology*; Glick B. R. and Thompson, J. E. (Eds.) (CRC Press, Inc., Boca Raton, 1993), pp. 67-88. In addition, expression vectors and in vitro culture methods for plant cell or tissue transformation and regeneration of plants are known in the art. See, e.g., Gruber et al., "Vectors for Plant Transformation" in Methods *in Plant Molecular Biology and Biotechnology*, Glick B. R. and Thompson, J. E. (Eds.) (CRC Press, Inc., Boca Raton, 1993), pp. 89-119.

A. *Agrobacterium*-Mediated Transformation

One method for introducing an expression vector into plants is based on the natural transformation system of *Agrobacterium*. See, e.g., Horsch et al., *Science*, 227:1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of plants. See, e.g., Kado, C. I., *Crit. Rev. Plant Sci.*, 10:1 (1991). Descriptions of *Agrobacterium* vector systems and methods for *Agrobacterium*-mediated gene transfer are provided by Gruber et al., supra; Miki et al., supra; and Moloney, et al., *Plant Cell Reports*, 8:238 (1989). See also U.S. Pat. No. 5,591,616.

B. Direct Gene Transfer

Despite the fact the host range for *Agrobacterium*-mediated transformation is broad, it is more difficult to transform some cereal crop species and gymnosperms via this mode of gene transfer, although success has been achieved in both rice and corn. See Hiei et al., The *Plant Journal*, 6:271-282 (1994); and U.S. Pat. No. 5,591,616. Other methods of plant transformation exist as alternatives to *Agrobacterium*-mediated transformation.

A generally applicable method of plant transformation is microprojectile-mediated (so-called "gene gun") transformation, in which DNA is carried on the surface of microprojectiles, typically 1 to 4 m in diameter. The expression vector is introduced into plant tissues with a biolistic device that accelerates the microprojectiles to typical speeds of 300 to 600 m/s, sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Technology*, 6:559-563 (1988); Sanford, J. C., *Physiol Plant*, 7:206 (1990); and Klein et al., *Biotechnology*, 10:268 (1992). Various target tissues may be bombarded with DNA-coated microprojectiles to produce transgenic plants, including, for example, callus (Type I or Type II), immature embryos, and meristematic tissue.

Another method for physical delivery of DNA to plants is sonication of target cells. Zhang et al., *Bio/Technology*, 9:996 (1991). Alternatively, liposome or spheroplast fusion has been used to introduce expression vectors into plants. Deshayes et al., *EMBO J.*, 4:2731 (1985); and Christou et al., *Proc Natl. Acad. Sci. U.S.A.*, 84:3962 (1987). Direct uptake of DNA into protoplasts, using $CaCl_2$) precipitation, polyvinyl alcohol, or poly-L-ornithine, has also been reported. Hain et al., *Mol. Gen. Genet.*, 199:161 (1985); and Draper et al., *Plant Cell Physiol.*, 23:451 (1982). Electroporation of protoplasts and whole cells and tissues has also been described. Donn et al., in Abstracts of VIIth International Congress on Plant Cell and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994).

Following transformation of rice target tissues, expression of a selectable marker gene allows preferential selection of transformed cells, tissues, or plants, using regeneration and selection methods known in the art.

These methods of transformation may be used for producing a transgenic inbred line. The transgenic inbred line may then be crossed with another inbred line (itself either transformed or non-transformed), to produce a new transgenic inbred line. Alternatively, a genetic trait that has been engineered into a particular rice line may be moved into another line using traditional crossing and backcrossing techniques. For example, backcrossing may be used to move an engineered trait from a public, non-elite inbred line into an elite inbred line, or from an inbred line containing a foreign gene in its genome into an inbred line or lines that do not contain that gene.

The term "inbred rice plant" should be understood also to include single gene conversions of an inbred line. Backcrossing methods can be used with the present invention to improve or introduce a characteristic into an inbred line.

Many single gene traits have been identified that are not regularly selected for in the development of a new inbred line, but that may be improved by crossing and backcrossing. Single gene traits may or may not be transgenic. Examples of such traits include male sterility, waxy starch, herbicide resistance, resistance for bacterial or fungal or viral disease, insect resistance, male fertility, enhanced nutritional quality, yield stability, and yield enhancement. These genes are generally inherited through the nucleus. Known exceptions to the nuclear genes include some genes for male sterility that are inherited cytoplasmically, but that still act functionally as single gene traits. Several single gene traits are described in U.S. Pat. Nos. 5,777,196; 5,948,957; and 5,969,212.

Deposit Information

A sample of the rice cultivar designated 'Addi Jo' was deposited with the Provasoli-Guillard National Center for Marine Algae and Microbiota, Bigelow Laboratory for Ocean Science, 60 Bigelow Drive, East Boothbay, Maine 04544, United States (NCMA) on 15 Dec. 2022, and was assigned NCMA Accession No. 202212066. This deposit was made under the Budapest Treaty.

Miscellaneous

The complete disclosures of all references cited in this specification are hereby incorporated by reference. In the event of an otherwise irreconcilable conflict, however, the present specification shall control.

What is claimed:

1. A rice plant of the variety 'Addi Jo', a representative sample of seeds of said variety 'Addi Jo' having been deposited under NCMA Accession No. 202212066.

2. A rice seed of the rice plant of claim 1, or a rice seed capable of producing said rice plant.

3. The seed of claim 2, wherein said seed is coated with a seed treatment or contains a seed treatment.

4. Pollen or an ovule of the plant of claim 1.

5. A tissue culture of regenerable cells or protoplasts produced from the rice plant of claim 1.

6. The tissue culture of claim 5, wherein said regenerable cells or protoplasts are produced from a tissue selected from the group consisting of embryos, meristematic cells, pollen, leaves, anthers, roots, root tips, flowers, seeds, and stems.

7. A method for producing rice plants, said method comprising planting a plurality of the rice seeds of claim 2 under conditions favorable for the growth of rice plants.

8. The method of claim 7, additionally comprising the step of producing rice seed from the resulting rice plants.

9. A method of producing a rice plant, said method comprising transforming the rice plant of claim 1 with one or more of: a transgene that confers herbicide tolerance, a transgene that confers insect resistance, a transgene that confers disease resistance, a transgene that encodes fructosyltransferase, a transgene that encodes levansucrase, a transgene that encodes alpha-amylase, a transgene that encodes invertase, a transgene that encodes a starch-branching enzyme, or a transgene that encodes an antisense sequence to stearyl-ACP desaturase.

10. A rice plant produced by the method of claim 9.

11. A method of introducing a desired trait into rice cultivar 'Addi Jo,' said method comprising the steps of:
(a) crossing 'Addi Jo' plants as recited in claim 1 with plants of another rice line expressing the desired trait, to produce progeny plants;
(b) selecting progeny plants that express the desired trait, to produce selected progeny plants;
(c) crossing the selected progeny plants with 'Addi Jo' plants to produce new progeny plants;
(d) selecting new progeny plants that express both the desired trait and some or all of the physiological and morphological characteristics of rice cultivar 'Addi Jo', to produce new selected progeny plants; and
(e) repeating steps (c) and (d) three or more times in succession, to produce selected higher generation backcross progeny plants that express both the desired trait and essentially all of the physiological and morphological characteristics of rice cultivar 'Addi Jo', as described in the VARIETY DESCRIPTION INFORMATION of the specification, determined at a 5% significance level, when grown in the same environmental conditions.

12. A rice seed from a progeny plant produced by the method of claim 11.

13. The method of claim 11, additionally comprising the step of planting a plurality of rice seed produced by selected higher generation backcross progeny plants under conditions favorable for the growth of rice plants.

14. A method for producing a herbicide-resistant rice plant, said method comprising crossing a first parent rice plant with a second parent rice plant; wherein the first parent rice plant is the rice plant of claim 1; wherein the second parent rice plant is tolerant to at least one herbicide; and wherein the resulting $F_1$ progeny rice plant is resistant to at least one herbicide.

15. An $F_1$ herbicide-resistant rice plant produced by the method of claim 14.

16. The method of claim 14, additionally comprising the step of producing rice seed from the resulting $F_1$ progeny rice plant.

17. A rice seed produced by the method of claim 16.

* * * * *